United States Patent
Marion et al.

(10) Patent No.: US 9,636,377 B2
(45) Date of Patent: May 2, 2017

(54) COMPOSITIONS AND METHODS FOR THE TREATMENT OF RETINAL DEGENERATION

(71) Applicant: UNIVERSITE DE STRASBOURG, Strasbourg (FR)

(72) Inventors: Vincent Marion, Schiltigheim (FR); Anaïs Mockel, Strasbourg (FR); Hélène Dollfus, Strasbourg (FR)

(73) Assignee: UNIVERSITE DE STRASBOURG, Strasbourg (FR)

( * ) Notice: Subject to any disclaimer, the term of this patent is extended or adjusted under 35 U.S.C. 154(b) by 0 days.

(21) Appl. No.: 14/380,493

(22) PCT Filed: Feb. 25, 2013

(86) PCT No.: PCT/EP2013/053724
§ 371 (c)(1),
(2) Date: Aug. 22, 2014

(87) PCT Pub. No.: WO2013/124484
PCT Pub. Date: Aug. 29, 2013

(65) Prior Publication Data
US 2015/0038432 A1 Feb. 5, 2015

Related U.S. Application Data

(60) Provisional application No. 61/602,863, filed on Feb. 24, 2012.

(51) Int. Cl.
*A61K 38/07* (2006.01)
*A61K 31/19* (2006.01)
*A61K 45/00* (2006.01)
*A61K 31/155* (2006.01)
*A61K 45/06* (2006.01)
*A61K 38/22* (2006.01)
*A61K 38/55* (2006.01)

(52) U.S. Cl.
CPC ............ *A61K 38/07* (2013.01); *A61K 31/155* (2013.01); *A61K 31/19* (2013.01); *A61K 38/2278* (2013.01); *A61K 38/55* (2013.01); *A61K 45/00* (2013.01); *A61K 45/06* (2013.01)

(58) Field of Classification Search
None
See application file for complete search history.

(56) References Cited

PUBLICATIONS

Adams et al. ("The Retinal Cilipathies" Review Article; Ophthalamic Genetics, 28; 113-125, 2007).*

Boyce, M., et al., "A Selective Inhibitor of eIF2a Dephosphorylation Protects Cells from ER Stress," *Science*, Feb. 11, 2005, vol. 307, pp. 935-939.
Di Sano, F., et al., "Endoplasmic Reticulum Stress Induces Apoptosis by an Apoptosome-dependent but Caspase 12-independent Mechanism," *The Journal of Biological Chemistry*, Feb. 3, 2006, vol. 281, No. 5, pp. 2693-2700.
Mendes, C.S., et al., "ER stress protects from retinal degeneration," *The EMBO Journal*, 2009, vol. 28, No. 9, pp. 1296-1307.
Nakagawa, T., et al., "Caspase-12 mediates endoplasmic-reticulum-specific apoptosis and cytotoxicity by amyloid-β," *Nature*, Jan. 6, 2000, vol. 403, pp. 98-103.
Shiraishi, H., et al., "ER stress-induced apoptosis and caspase-12 activation occurs downstream of mitochondrial apoptosis involving Apaf-1," *Journal of Cell Science*, 2006, vol. 119, No. 19, pp. 3958-3966.
Tsaytler, P., et al., "Selective Inhibition of a Regulatory Subunit of Protein Phosphatase 1 Restores Proteostasis," *Science*, Apr. 1, 2011, vol. 332, pp. 91-94.
Walter, P., et al., "The Unfolded Protein Response: From Stress Pathway to Homeostatic Regulation," *Science*, Nov. 25, 2011, vol. 334, pp. 1081-1086.
Yoneda, T., et al., "Activation of Caspase-12, an Endoplastic Reticulum (ER) Resident Caspase, through Tumor Necrosis Factor Receptor-associated Factor 2-dependent Mechanism in Response to the ER Stress," *The Journal of Biological Chemistry*, Apr. 27, 2001, vol. 276, No. 17, pp. 13935-13940.
Zaghloul, N.A., et al., "Mechanistic insights into Bardet-Biedl syndrome, a model ciliopathy," *Journal of Clinical Investigation*, Mar. 2009, vol. 119, No. 3, pp. 428-437.
Griciuc, A. et al. "ER stress in retinal degeneration: a target for rational therapy?" *Trends in Molecular Medicine*, Aug. 1, 2011, pp. 442-451, vol. 17, No. 8.
Yang, L.-P. et al. "Endoplasmic Reticulum Stress Is Activated in Light-Induced Retinal Degeneration" *Journal of Neuroscience Research*, Mar. 1, 2008, pp. 910-919, vol. 86, No. 4.
Shen, Y. et al. "Effect of Guanabenz on Rat AMD Models and Rabbit Choroidal Blood Flow" *The Open Ophthalmology Journal*, Jan. 1, 2011, pp. 27-31, vol. 5.
Bown, C. D. et al. "Regulation of ER stress proteins by valproate: therapeutic implications" *Bipolar Disorders*, Jun. 14, 2002, pp. 145-151, vol. 4.
Clemson, C. M. et al. "Therapeutic potential of valproic acid for retinitis pigmentosa" *British Journal of Ophthalmology*, Jan. 1, 2011, pp. 89-93, vol. 95, No. 1.
Mockel, A. et al. "Pharmacological Modulation of the Retinal Unfolded Protein Response in Bardet-Biedl Syndrome Reduces Apoptosis and Preserves Light Detection Ability" *Journal of Biological Chemistry*, Oct. 1, 2012, pp. 37483-37494, vol. 287, No. 44.
Written Opinion in International Application No. PCT/EP2013/053724, Apr. 15, 2013, pp. 1-9.

(Continued)

*Primary Examiner* — James H Alstrum Acevedo
*Assistant Examiner* — Tara Martinez
(74) *Attorney, Agent, or Firm* — Saliwanchik, Lloyd & Eisenschenk

(57) ABSTRACT

The present invention relates to a pharmaceutical composition comprising an inhibitor of eIF2α, a compound increasing the expression and/or activity of protein BiP and/or an inhibitor of Caspase-12, preferably an inhibitor of eIF2α and a compound increasing the expression and/or activity of protein BiP. The present invention also relates to pharmaceutical compositions and methods for treating retinal degeneration related to ciliary dysfunction.

5 Claims, 18 Drawing Sheets
(15 of 18 Drawing Sheet(s) Filed in Color)

(56) References Cited

PUBLICATIONS

Fu, H. et al. "Overexpression of endoplasmic reticulum-resident chaperone attenuates cardiomyocyte death induced by proteasome inhibition" *Cardiovascular Research*, 2008, pp. 600-610, vol. 79.

Ou, L. et al. "Apoptosis induced by t10,c12-conjugated linoleic acid is mediated by an atypical endoplasmic reticulum stress response" *Journal of Lipid Research*, 2008, pp. 985-994, vol. 49.

Auner, H. W. etal. "The life span of short-lived plasma cells is partly determined by a block on activation of apoptotic caspases acting in combination with endoplasmic reticulum stress" *Blood*, Nov. 4, 2010, pp. 3445-3455, vol. 116, No. 18.

* cited by examiner

| | BiP level | peIF2α level | CHOP10 level | ONL length (μm) | % ONL thickening | a wave amplitude (μV) | b wave amplitude (μV) |
|---|---|---|---|---|---|---|---|
| untreated | / | / | / | 37 ± 2 | / | 18 ± 2 | 131 ± 14 |
| sVPA | = | = | ↘ | 44 ± 3 | 131% | 40 ± 4 | 195 ± 25 |
| sGBZ | ↘ | ↗ | = | 45 ± 1 | 136% | 43 ± 3 | 162 ± 9 |
| GMn | = | = | ↗ | 52 ± 1 | 152% | 48 ± 6 | 195 ± 20 |

Figure 18

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Xbp1 forward primer

<400> SEQUENCE: 1
ttacgggaga aaactcacgg c                                             21

```
<210> SEQ ID NO 2
<211> LENGTH: 22
<212> TYPE: DNA
<213> ORGANISM: Artificial Sequence
<220> FEATURE:
<223> OTHER INFORMATION: Xbp1 reverse primer

<400> SEQUENCE: 2
gggtccaact tgtccagaat gc                                            22

<210> SEQ ID NO 3
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: (OMe)-fluoromethyl ketone

<400> SEQUENCE: 3

Ala Thr Ala Asp
1
```

COMPOSITIONS AND METHODS FOR THE TREATMENT OF RETINAL DEGENERATION

CROSS-REFERENCE TO RELATED APPLICATIONS

This application is the U.S. national stage application of International Patent Application No. PCT/EP2013/053724, filed Feb. 25, 2013, which claims the benefit of U.S. Provisional Patent Application No. 61/602,863, filed Feb. 24, 2012.

The Sequence Listing for this application is labeled "Seq-List-replace.txt" which was created on Apr. 12, 2016 and is 1 KB. The entire content of the sequence listing is incorporated herein by reference in its entirety.

FIELD OF THE INVENTION

The present invention relates to the field of medicine, in particular to the treatment of retinal degeneration, in particular retinal degeneration related to ciliary dysfunction.

BACKGROUND OF THE INVENTION

Retinal degeneration is a very common clinical feature in ciliopathies, a group of rare genetic disorders originating from a defect in the primary cilium, an organelle ubiquitously expressed in the human body. The photoreceptor cell is structured with two segments connected by a modified cilium, the so-called connecting cilium that acts as a protein highway allowing protein transport between the two segments required for efficient light detection and transduction. Ciliopathies therefore impact protein transport from the inner to the outer segment and backwards, inducing retinitis pigmentosa. The onset is usually during early childhood and leads to major visual impairment early on with a major impact on everyday life and social integration.

This retinal degeneration mechanism is observed either in isolated retinitis pigmentosa (such as Leber's Congenital Amaurosis or X-linked retinitis pigmentosa) or also in syndromic conditions like Bardet-Biedl Syndrome (BBS) or Alström syndrome (ALMS), both emblematic ciliopathies cardinally characterized by retinitis pigmentosa. Among all the biological processes that can be implied, a defect in the functioning of the connecting cilia represents more than 20% of all cases of retinitis pigmentosa, which is overall a very high rate for a common pathogenesis mechanism.

Treatment for inherited retinal dystrophies has progressed at a regular speed in the last decade. However, presently there is no curative approach available and no satisfactory palliative approach that actually helps to preserve the vision or at least slow the retinal defects. Treatments mainly focus on reducing the symptoms (tinted glasses, low vision aids) and preventing the complications (cataract surgery, cystoid macular edema).

To date, a dozen studies or trials are declared and currently under way using various approaches: pharmacological, tissue engineering, gene therapy and prosthetic devices. Gene therapy is one of the most advanced fields to date as trials are currently being performed on human beings in various countries, especially for the most emblematic RPE65 gene therapy projects. Due to the high genetic heterogeneity and the multiple biological pathways involved in retinitis pigmentosa, the diversity of strategies to find treatment remains pertinent. A couple of gene therapy projects for ciliopathy related retinal degenerations are currently being undertaken: RPGR in dogs (Beltran et al., 2011) and BBS4 in mice (Simons et al., 2011).

However, the retinal degeneration occurs in most cases very early in childhood and early gene therapy injections may be dangerous in terms of inflammatory reactions known to be acute in very young children. Accordingly, there is a significant need for a pharmacological treatment that could slow the retinal degeneration for preserving the photoreceptor cells in various ciliopathies and postponing the use of gene therapy.

SUMMARY OF THE INVENTION

Retinal ciliopathies represent a class of genetic diseases wherein the connecting cilium of the photoreceptors is defective. This defect of genetic origin prevents efficient protein transport between the biosynthetic active inner segment and the light-sensitive outer segment. This ciliary traffic jam has been reported to induce endoplasmic reticulum (ER) stress due to protein accumulation in the inner segment of the photoreceptor (Lin et al., 2007; Yang et al., 2007). ER stress induces a coordinated response pathway: the unfolded protein response (UPR) (Griciuc et al., 2011; Walter and Ron, 2011). The UPR detects and manages protein-folding stress by activation of two balanced responses: a protective one and an apoptotic one.

In the retina, the photoreceptor cell is responsible for the first step of phototransduction. It is composed of a biosynthetically active inner segment and a light-sensitive outer segment linked by a modified primary cilium known as the connecting cilium. Retinal degeneration related to ciliary dysfunction can be an isolated feature or a part of a syndrome such as Bardet-Biedl syndrome (BBS).

The inventors have herein shown that the ciliary defect in BBS models induced photoreceptor apoptosis via endoplasmic reticulum stress due to protein accumulation in the inner segment. Once the triggered pathway was clearly identified, they developed a therapeutic strategy of unfolded protein response modulation. They have achieved protection of photoreceptors against apoptosis and maintained the function of the retina in Bbs12$^{-/-}$ mice. They have herein reported the proof of principle for retinal degeneration slowdown in a mouse model of BBS using ER stress-modulating drugs. Although these drugs, i.e., the inhibitor of eIF2α, the compound increasing the expression and/or activity of protein BiP and the inhibitor of caspase-12, have shown some effects when tested separately, the combination of the two or three molecules has proven to be far more effective in preventing apoptosis. Remarkably, the combination of these drugs has also allowed the inventors to reduce the doses administered to the in vivo models, limiting to the maximum any possible side effects.

Accordingly, in a first aspect, the present invention concerns a pharmaceutical composition comprising an inhibitor of eIF2α, a compound increasing the expression and/or activity of protein BiP, and a pharmaceutically acceptable carrier and/or excipient.

The inhibitor of eIF2-α may be selected from the group consisting of guanabenz, tautomycin, tautomycetin, calyculin A, salubrinal, a compound inhibiting the formation of the PP1/GADD34 complex and a nucleic acid molecule specifically interfering with PP1 or GADD34 expression.

Preferably, the inhibitor of eIF2-α is an inhibitor of GADD34, and more preferably the inhibitor of eIF2-α is guanabenz.

The compound increasing the expression and/or activity of protein BiP may be selected from the group consisting of valproic acid or a derivative thereof, trichostatin A, Preferably, the compound increasing the expression and/or activity of protein BiP is valproic acid or a derivative thereof such as 2-ene-valproic acid, and more preferably the compound increasing the expression and/or activity of protein BiP is valproic acid.

The pharmaceutical composition according to the invention may further comprise an inhibitor of caspase-12, preferably selected from the group consisting of a peptide targeting the catalytical site of caspase-12, a peptide preventing the cleavage of procaspase-12 and a nucleic acid molecule specifically interfering with caspase-12 expression. In particular, the inhibitor of caspase-12 may be a peptide targeting the catalytical site of caspase-12, preferably a peptide of formula Ala-Thr-Ala-Asp(OMe)-fluoromethyl ketone (SEQ ID NO: 3).

The pharmaceutical composition according to the invention may further comprise at least one additional therapeutic agent, preferably selected from the group consisting of a chemotherapeutic agent, a corticosteroid, an antibiotic, an analgesic, an alpha-adrenergic blocker, an alpha-adrenergic agonist, a beta-adrenergic agonist, an anticholinergic, an inhibitor of 5-alpha-reductase, an androgen, an immunomodulator, an immunosuppressant, an anti-angiogenic such as anti-VEGF, anti-FGF, anti-HGF and anti-EFG, a leukotriene modifier, an aminosalicylate, an anesthetic, a non-steroidal anti-inflammatory, an antiparasitic, a therapy of the solubilized interleukin receptor, a cytotoxin, an antioxidant, and any combinations thereof.

The present invention also concerns the pharmaceutical composition according to the invention for use as a drug, and more particularly for use in the treatment of retinal degeneration related to ciliary dysfunction.

The retinal degeneration related to ciliary dysfunction may be induced by a ciliopathy selected from the group consisting of Bardet-Biedl syndrome, Senior-Loken syndrome, Joubert syndrome, Mainzer-Saldino syndrome, Sensenbrenner syndrome, Jeune syndrome, Meckel-Gruber syndrome, Alström syndrome, MORM syndrome, Leber's congenital amaurosis caused by mutation in a ciliary gene and X-linked retinitis pigmentosa caused by mutation in the RPGR gene.

The present invention also concerns a pharmaceutical composition comprising an inhibitor of eIF2α, a compound increasing the expression and/or activity of protein BiP, and a pharmaceutically acceptable carrier and/or excipient, to be used in combination with an inhibitor of caspase-12.

The present invention further concerns a product containing an inhibitor of eIF2α and a compound increasing the expression and/or activity of protein BiP, and optionally an inhibitor of caspase-12, as a combined preparation for simultaneous, separate or sequential use in the treatment of retinal degeneration related to ciliary dysfunction.

In particular, the product may contain an inhibitor of eIF2α, a compound increasing the expression and/or activity of protein BiP and an inhibitor of caspase-12.

Preferably, the inhibitor of eIF2α is guanabenz, and/or the compound increasing the expression and/or activity of protein BiP is valproic acid, and/or the inhibitor of caspase-12 is the peptide Ala-Thr-Ala-Asp(OMe)-fluoromethyl ketone (SEQ ID NO: 3).

Preferably, the pharmaceutical composition or the product according to the invention is suitable for topical, oral, intradermal, parenteral and/or intraocular administration.

More preferably, the pharmaceutical composition or the product according to the invention is suitable for ophthalmic administration, preferably for topical ocular or peri-ocular administration.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 18: Comparison of UPR-related targets level, ONL length (mm±SEM) and thickening and "a and b waves" amplitudes (μV±SEM at 1 cd*s/m$^2$) in the Bbs12$^{-/-}$ retinas from animals receiving sVPA, sGBZ or GIVin compared to untreated animals. sVPA: systemic valproic acid 5 mg/ml; sGBZ: systemic guanabenz 50 μM; GIVin: topical GBZ 7.5 μM+topical INH 500 μM+systemic VPA 5 mg/ml.

DETAILED DESCRIPTION OF THE INVENTION

Figure 1:
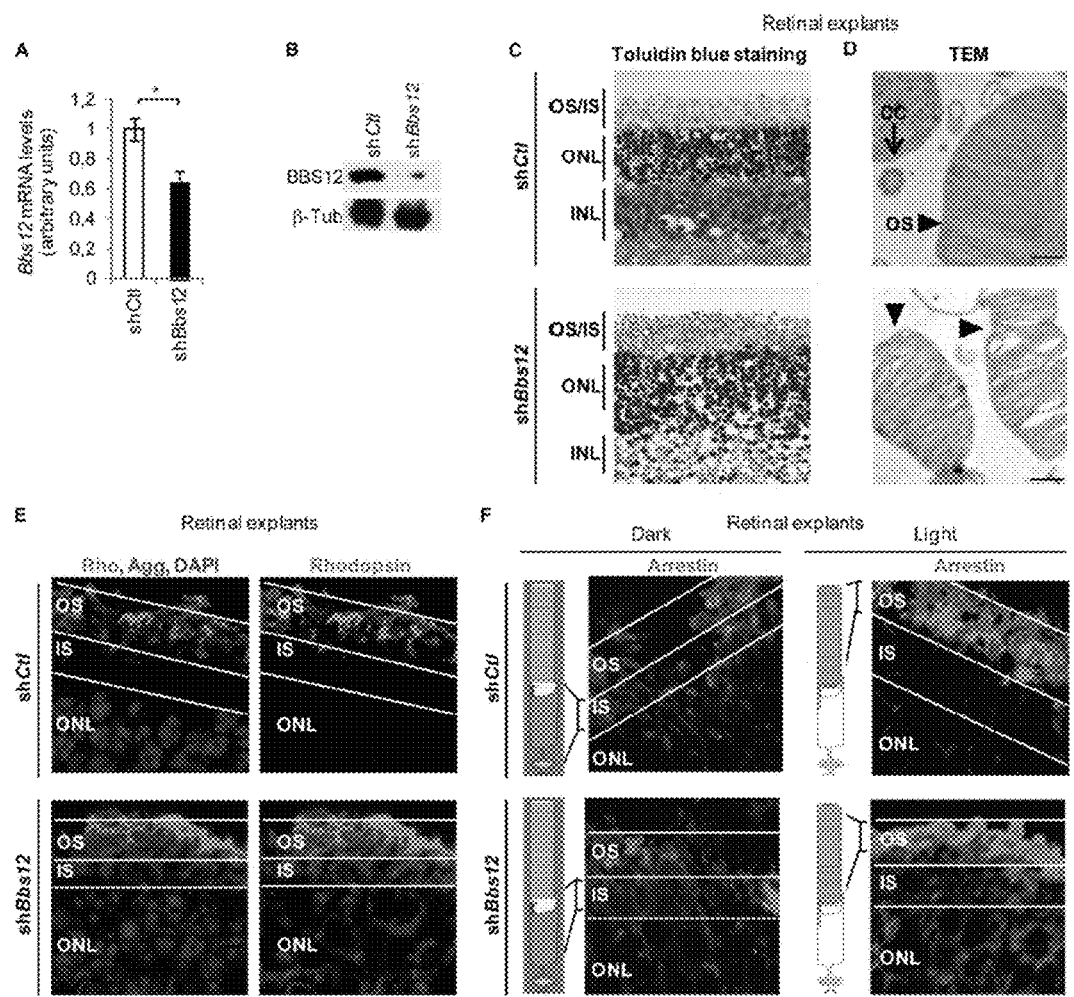
FIG. 1 Bbs12 depletion in retinal explants induces photoreceptor dysmorphy. (a) Expression analysis of Bbs12 in shCtl and shBbs12 treated explants (n=3). shCtl, control shRNA; shBbs12, Bbs12-shRNA. *, p<0.01. (b) BBS12 protein level in shCtl and shBbs12 treated explants. Immunodetection of BBS12 and β-tubulin as loading control. (c) Toluidine blue stained sections of treated explants. Scale bars 50 μm. INL, inner nuclear layer. (d) Transmission electron microscopy pictures showing photoreceptors OS and connecting cilium (CC) of shCtl-treated (upper panel) and shBbs12-treated (lower panel) explants. Scale bars, 500 nm. (e) Immunostaining of Rhodopsin with DAPI and OS counterstaining using Agglutinin in treated explants. Scale bars, 15 μm. (f) Immunostaining of Arrestin in dark (left panel) and light (right panel) conditions in shCtl and shBbs12 treated explants; cartoon represents the expected localization of Arrestin in both conditions. Scale bars 15 μm.

Worldwide, retinitis pigmentosa (RP) is the most common cause of genetically determined blindness. Bardet-Biedl syndrome (BBS, OMIM 290900) is a genetic disease involving syndromic RP due to photoreceptor cells loss. BBS is characterized by early onset of RP, polydactyly, obesity, renal dysfunction, hypogonadism and cognitive impairment (Mockel et al., 2011). BBS is a heterogeneous condition with at least 17 genes identified to date: BBS1 to BBS17. All the BBS genes have been related to cilium biogenesis and/or function (Fliegauf et al., 2007). Functionally, seven BBS proteins (BBS1, 2, 4, 5, 7, 8 and 9) form a stable complex named the BBSome involved in vesicular trafficking to the ciliary membrane (Nachry et al., 2007). A chaperonin complex including BBS6, 10 and 12 (the chaperonin-like BBS proteins) mediates the BBSome assembly (Seo et al., 2010). The photoreceptor's connecting cilium (CC) is a modified primary cilium. It links the biosynthetically active inner segment (IS) to the light sensitive outer segment (OS).

Connecting cilium is essential for outer segment growth and maintenance because it is the only transport corridor for functional and structural proteins needed in the OS.

BBS knock-out mice models have been generated for several BBS genes (Bbs1$^{M380R/M380R}$, Bbs2$^{-/-}$, Bbs3L$^{-/-}$, Bbs4$^{-/-}$ and Bbse) (Fath et al., 2005; Nishimura et al., 2004; Mykytyn et al., 2004; Davis et al., 2007; Pretorius et al., 2010). At birth, all mutant mice present a correct retinal lamination and a correct photoreceptor development including a connecting cilium and an outer segment formation. Despite its correct development, the outer segment fails to persist as these mice present an OS degradation and photoreceptor cell death. Interestingly, Bbs1$^{M380R/M380R}$, Bbs2$^{-/-}$, Bbs4$^{-/-}$ and Bbs6$^{-/-}$ mice have Rhodopsin accumulation in the outer nuclear layer (ONL) and in the inner segment. The Bbs4$^{-/-}$ mouse has defects in the light-dependent transport of both Arrestin and Transducin (Abd-El-Barr et al., 2007). This links BBS proteins not only to vesicle trafficking but also directly to intraciliary transport (ICT), at least in the photoreceptor. One of the most important proteins transported along the connecting cilium is Rhodopsin. Some mutations in the Rhodopsin gene inducing its misfolding and accumulation in the inner segment lead to photoreceptor apoptosis. Misfolded Rhodopsin accumulation was recently shown to induce cell death via endoplasmic reticulum (ER) stress (Tam et al., 2006). The latter induces a coordinated response pathway termed the unfolded protein responses (UPR) (Griciuc et al., 2011). The UPR detects and manages protein-folding stress by activating two balanced responses, a protective one and an apoptotic one. Unfolded protein accumulation in the ER leads to its cisternae dilation and sensing of aggregated proteins by molecular chaperones. Binding Immunoglobulin heavy chain Protein (BiP) is an ER resident chaperone and is a sensor of ER stress (Kosmaoglou et al., 2008). It works to restore folding of proteins. BiP also activates eukaryotic initiation factor 2 alpha (eIF2α) kinase: PRKR-like Endoplasmic Reticulum Kinase (PERK). This step forms part of the adaptive response of UPR and it results in a reduction of cap-dependent protein synthesis in order to alleviate the protein load in the ER. Indeed, it allows the activation of an alternative transcription and translation pathway to mediate the adaptative response. One key transcription factor is XBP1. ER stress induces an alternative splicing of Xbp1 leading to the expression of its short isoform responsible for the transcription of a set of genes involved in UPR response including the transcription factor C/EBP Homologous Protein (Chop10). CHOP10 is important for the balance between apoptotic and protective pathways. If homeostasis is not re-established, the proapoptotic response is promoted and leads to apoptosis via caspase-12 It is ER-located and is specifically activated if caspase cascade is required (Yang et al., 2007). Its activation upon prolonged ER stress induces effector caspase activation: caspase-3, -6 and -7.

ER stress modulation can be an emerging therapeutic option in retinal degeneration provided that the triggered pathway is clearly identified. The inventors have herein investigated the signalling cascade in the UPR that ultimately leads to photoreceptor death using Bbs12 depleted retinal explants and Bbs12$^{-/-}$ mouse models. Then, they have developed a therapeutic strategy of UPR modulation. They have achieved protection of photoreceptor cells against apoptosis and maintained function of the retina in BBS-induced retinal degeneration.

The inventors have thus herein demonstrated that it is possible to pharmacologically modulate the UPR in the photoreceptors in order to prevent apoptosis of these photoreceptors. The inventors have investigated the signalling cascade involved in the unfolded protein response and have highlighted three main targets to develop a therapeutic strategy for treating retinal ciliopathies, namely GADD34, BiP and caspase-12.

GADD34, also named protein phosphatase 1 regulatory subunit 15A or PPP1R15A (geneID: 23645), is an eukaryotic initiation factor 2α (eIF2α) phosphatase. This enzyme interacts with protein phosphatase 1 (PP1) to dephosphorylate, and thus activate, eIF2α and thus regulates CAP-dependent protein translation.

BiP (Binding Immunoglobulin heavy chain Protein), also named heat shock 70 kDa protein 5, HSPA5, MIF2 or GRP78 (GeneID: 3309), is a molecular chaperone localized in the lumen of the ER. Its function is to sequester nascent proteins, to restore folding of proteins and to activate eIF2α kinase.

Caspase-12, also named CASP-12 (GeneID: 100506742), is a cysteine protease specifically activated by ER stress and acting as a trigger for the effector caspases which launch the apoptotic final step.

The invention thus consists of using a modulator or a combination of two or three modulators for specific UPR actors as described above to maintain cell homeostasis, prevent cellular death and preserve the light detection ability of the retina.

Accordingly, in a first aspect, the present invention concerns a pharmaceutical composition comprising an inhibitor of eIF2α and/or a compound increasing the expression and/or activity of protein BIP and/or an inhibitor of caspase-12.

Preferably, the pharmaceutical composition comprises at least two compounds selected from the group consisting of an inhibitor of eIF2α and/or a compound increasing the expression and/or activity of protein BIP and/or an inhibitor of caspase-12.

In a preferred embodiment, the pharmaceutical composition comprises an inhibitor of eIF2α and a compound increasing the expression and/or activity of protein BIP.

As used herein, the term "inhibitor" refers to a compound inhibiting or reducing the activity or the expression of a protein, or a compound preventing the activation of said protein.

The term "eIF2α inhibitor", as used herein, refers to a compound inhibiting or reducing the activity of the translation initiation factor eIF2α or its expression, or a compound preventing the activation of eIF2α, for example by reducing or blocking its dephosphorylation. The activity of an eIF2α inhibitor can be easily assayed by any method known in the art. For example, the inhibitory activity can be assayed through the measure of the quantity of active and inactive forms of eIF2α. The quantity of active and inactive forms of eIF2α may be determined using immunological methods, in particular using commercial antibodies specific to eIF2α and phosphorylated forms of eIF2α as detailed in the experimental section.

In an embodiment, the eIF2α inhibitor is a compound that prevents the activation of eIF2α. The activation of eIF2α may be prevented by reducing or blocking its dephosphorylation. In particular, the compound may be an inhibitor of the catalytic subunit of protein phosphatase 1 (PP1), an inhibitor of GADD34 or an inhibitor of the PP1/GADD34 complex.

Examples of inhibitors of the catalytic subunit of PP1 include, but are not limited to, tautomycin, tautomycetin (Mitsuhashi et al., 2003), calyculin A and a nucleic acid molecule specifically interfering with PP1 expression.

Examples of inhibitors of GADD34 include, but are not limited to, guanabenz (Tsaytler et al., 2011) and a nucleic acid molecule specifically interfering with GADD34 expression. In particular, the activity of GADD34 can be repressed or inhibited by guanabenz (GBZ).

Examples of inhibitors of the PP1/GADD34 complex include, but are not limited to, salubrinal and a compound, e.g., a peptide, inhibiting the formation of the PP1/GADD34 complex, i.e., a compound that is able to compete with GADD34 to form a complex with PP1 and thereby render said complex non-functional. Such compounds are described for example in the international patent application WO 2008/028965.

Thus, in a particular embodiment, the eIF2α inhibitor is a compound that prevents the activation of eIF2α and is selected from the group consisting of guanabenz, tautomycin, tautomycetin, calyculin A, salubrinal, a compound inhibiting the formation of the PP1/GADD34 complex and a nucleic acid molecule specifically interfering with PP1 or GADD34 expression.

In a preferred embodiment, the eIF2α inhibitor is an inhibitor of GADD34. More preferably, the eIF2α inhibitor is guanabenz. Guanabenz (CAS number 5051-62-7) is an alpha-2 selective adrenergic agonist currently used as an antihypertensive drug.

As used herein, the term "nucleic acid molecule specifically interfering with PP1 or GADD34 expression" refers to a nucleic acid molecule which is able to reduce or to suppress the expression of gene coding for PP1 or GADD34 in a specific way. The interfering nucleic acid is preferably selected from the group consisting of RNAi, antisense and ribozyme molecules.

In particular, the term "RNAi molecule" refers to any RNA which is capable of down-regulating the expression of the targeted protein. It encompasses small interfering RNA (siRNA), double-stranded RNA (dsRNA), single-stranded RNA (ssRNA), micro-RNA (miRNA), and short hairpin RNA (shRNA) molecules.

Antisense nucleic acid molecules can be complementary to all or part of a sense nucleic acid encoding the targeted polypeptide, e.g., complementary to the coding strand of a double-stranded cDNA molecule or complementary to an mRNA sequence, and are thought to interfere with the translation of the target mRNA. Methods for designing, producing and administering RNAi and antisense molecules are well known by the skilled person.

Ribozymes are catalytic RNA molecules with ribonuclease activity which are capable of cleaving a single-stranded nucleic acid, such as an mRNA, to which they have a complementary region. Thus, ribozymes can be used to catalytically cleave mRNA transcripts to thereby inhibit translation of the protein encoded by the mRNA. Ribozyme molecules specific for a target can be designed, produced, and administered by methods commonly known to the art.

The compound increasing the expression and/or activity of protein BIP may be selected from the group consisting of valproic acid or a derivative thereof such as 2-ene-valproic acid, trichostatin A (Shi et al., 2007), lithium (Hiroi et al., 2005), 1-(3,4-dihydroxy-phenyl)-2-thiocyanate-ethanone (Kudo et al., 2008) and exendin-4 (Cunha et al., 2009).

Preferably, said compound increases the expression and the activity of protein BIP. The expression and activity of BiP can be increased for example by valproic acid (VPA) as demonstrated in the experimental section. Thus, in a preferred embodiment, the compound increasing the expression and/or activity of protein BiP is valproic acid or a derivative thereof. In particular, the derivative may be 2-ene-valproic acid. Preferably the compound increasing the expression and/or activity of protein BiP is valproic acid. Valproic acid (CAS number 99-66-1) is a fatty acid with anticonvulsant properties currently used in the treatment of epilepsy. Valproic acid is typically supplied in the sodium salt form.

By combining the effects of the repression of the enzymatic activities of GADD34 and caspase-12 with the upregulation of BiP gene expression and its protein activity, the inventors have achieved significant reduction in cellular death of the photoreceptor apoptosis and, thereby, maintained light detection ability of the retina in a model of syndromic retinal ciliopathy, Bardet-Biedl syndrome (BBS).

Thus, in an embodiment, the pharmaceutical composition of the invention comprises an inhibitor of caspase-12, preferably in combination with an inhibitor of eIF2α and/or a compound increasing the expression and/or activity of protein BIP.

In a particular embodiment, the pharmaceutical composition of the invention comprises an inhibitor of eIF2α, a compound increasing the expression and/or activity of protein BIP and an inhibitor of caspase-12.

The inhibitor of caspase-12 may be a peptide targeting the catalytical site of the enzyme, a peptide preventing the cleavage of procaspase-12 or a nucleic acid molecule specifically interfering with caspase-12 expression.

The nucleic acid molecule specifically interfering with caspase-12 expression is a nucleic acid molecule which is able to reduce or to suppress the expression of gene coding for caspase-12 in a specific way. As defined above for PP1 and GADD34, the interfering nucleic acid is preferably selected from the group consisting of RNAi, antisense and ribozyme molecules. In particular, the nucleic acid molecule may be a ribozyme as described in Jiang et al., 2008.

In a preferred embodiment, the activity of caspase-12 is repressed by a small peptide targeting the catalytical site of the caspase-12 enzyme and having the formula Ala-Thr-Ala-Asp(OMe)-fluoromethyl ketone (SEQ ID NO: 3). In particular, said peptide may have the formula benzyloxycarbonyl-Ala-Thr-Ala-Asp(OMe)-fluoromethyl ketone (SEQ ID NO: 3). This peptide is commercially available from several suppliers.

For in vitro applications, cells are incubated in a suitable culture medium comprising a compound preventing the activation of eIF2α and/or an inhibitor of caspase-12 and/or a compound increasing the expression and/or activity of protein BiP.

The pharmaceutical composition of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. In particular, the pharmaceutical composition may comprise one or several pharmaceutically acceptable excipients and/or carriers.

Possible pharmaceutical compositions include those suitable for ophthalmic (including intraocular, topical ocular or peri-ocular), oral, rectal, topical (including transdermal, buccal and sublingual), or parenteral (including subcutaneous, intramuscular, intraspinal, intravenous and intradermal) administration. For these formulations, conventional excipients can be used according to techniques well known by those skilled in the art.

The compositions for parenteral or ophthalmic administration are generally physiologically compatible sterile solutions or suspensions which can optionally be prepared immediately before use from solid or lyophilized form. Adjuvants such as a local anesthetic, preservative and buffering agents can be dissolved in the vehicle and a surfactant or wetting agent can be included in the composition to facilitate uniform distribution of the active ingredient.

For oral administration, the composition can be formulated into conventional oral dosage forms such as tablets, capsules, powders, granules and liquid preparations such as syrups, elixirs, and concentrated drops. Non-toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

In particular, suitable routes of administration are topically, orally, intradermally, parenterally or intraocularly. In particular guanabenz and valproic acid may be administered orally or intraocularly, and the peptide inhibiting caspase-12 may be administered intraocularly.

Preferably, the pharmaceutical composition of the invention is suitable for ophthalmic administration, in particular for intraocular, topical ocular or peri-ocular administration, more preferably for topical ocular or peri-ocular administration.

Pharmaceutical compositions according to the invention may be formulated to release the active drugs substantially immediately upon administration or at any predetermined time or time period after administration.

Pharmaceutical compositions may comprise one or several inhibitors of eIF2α and/or one or several compounds increasing the expression and/or the activity of protein BiP, and/or one or several inhibitors of caspase-12, associated with pharmaceutically acceptable excipients and/or carriers. These excipients and/or carriers are chosen according to the form of administration as described above.

The pharmaceutical compositions may also comprise at least one other therapeutic agent. In particular, said therapeutic agent may be selected from the group consisting of a chemotherapeutic agent, a corticosteroid, an antibiotic, an analgesic, an alpha-adrenergic blocker, an alpha-adrenergic agonist, a beta-adrenergic agonist, an anticholinergic, an inhibitor of 5-alpha-reductase, an androgen, an immunomodulator, an immunosuppressant, an anti-angiogenic such as anti-VEGF, anti-FGF, anti-HGF and anti-EFG, a leukotriene modifier, an aminosalicylate, an anesthetic, a non-steroidal anti-inflammatory, an antiparasitic, a therapy of the solubilized interleukin receptor, a cytotoxin, an antioxidant, and any combinations thereof.

Pharmaceutical compositions of the invention can be administered continuously by infusion, by bolus injection, or, where the compositions are sustained-release preparations, by methods appropriate for the particular preparation.

The amount of the inhibitor of eIF2α, the compound increasing the expression and/or the activity of protein BiP, and/or the inhibitor of caspase-12 to be administered has to be determined by standard procedure well known by those of ordinary skill in the art. The physiological data of the patient (e.g., age, size, and weight) and the routes of administration have to be taken into account to determine the appropriate dosage. The appropriate dosage of each compound may also vary if the pharmaceutical comprises only one compound or a combination of two or three compounds selected from the group consisting of an inhibitor of eIF2α, a compound increasing the expression and/or the activity of protein BiP and an inhibitor of caspase-12, in particular the combination of an inhibitor of eIF2α and a compound increasing the expression and/or the activity of protein BiP.

The pharmaceutical composition of the invention may be administered as a single dose or in multiple doses. Each unit dosage may contain, for example, from 10 ng to 20 mg, preferably from 10 ng to 1 mg, per kg of body weight of an inhibitor of eIF2α, from 10 ng to 50 mg, preferably from 10 ng to 1 mg, per kg of body weight of a compound increasing the expression and/or the activity of protein BiP, and/or from 1 ng to 1 mg, preferably from 1 ng to 100 µg, per kg of body weight of an inhibitor of caspase-12. In particular, each unit dosage may contain, for example, from 50 ng to 1.6 g, preferably from 50 ng to 80 mg, of an inhibitor of eIF2α, from 50 ng to 4 g, preferably from 50 ng to 80 mg, of a compound increasing the expression and/or the activity of protein BiP, and/or from 5 ng to 80 mg, preferably from 5 ng to 8 mg, of an inhibitor of caspase-12. The unit dosage may be adapted according to the age of the patient, in particular if the intended use is a pediatric use.

In a preferred embodiment, the pharmaceutical composition comprises guanabenz and valproic acid, and optionally the peptide Ala-Thr-Ala-Asp(OMe)-fluoromethyl ketone (SEQ ID NO: 3).

Preferably, each unit dosage contains from 10 ng to 500 µg/kg of body weight of guanabenz, from 10 ng to 500 µg/kg of body weight of valproic acid, and optionally from 1 ng to 50 µg/kg of body weight of the peptide Ala-Thr-Ala-Asp(OMe)-fluoromethyl ketone (SEQ ID NO: 3). In particular, each unit dosage may contain from 50 ng to 40 mg of guanabenz, from 50 ng to 40 mg of valproic acid, and optionally from 5 ng to 4 mg of the peptide Ala-Thr-Ala-Asp(OMe)-fluoromethyl ketone (SEQ ID NO: 3). The unit dosage may be adapted according to the age of the patient, in particular if the intended use is a pediatric use.

The present invention also relates to a pharmaceutical composition comprising an inhibitor of eIF2α, preferably guanabenz, and a compound increasing the expression and/or activity of protein BiP, preferably valproic acid, for use in combination with an inhibitor of caspase-12, preferably the peptide Ala-Thr-Ala-Asp(OMe)-fluoromethyl ketone (SEQ ID NO: 3). The present invention also relates to a pharmaceutical composition comprising an inhibitor of eIF2α, preferably guanabenz, for use in combination with a compound increasing the expression and/or activity of protein BiP, preferably valproic acid, and optionally an inhibitor of caspase-12, preferably the peptide Ala-Thr-Ala-Asp(OMe)-fluoromethyl ketone (SEQ ID NO: 3). The present invention further relates to a pharmaceutical composition comprising an inhibitor of eIF2α, preferably guanabenz, and/or an inhibitor of caspase-12, preferably the peptide Ala-Thr-Ala-Asp(OMe)-fluoromethyl ketone (SEQ ID NO: 3), for use in combination with a compound increasing the expression and/or activity of protein BiP, preferably valproic acid. In particular, these combinations are for use as a drug, preferably for use in the treatment of retinal degeneration related to ciliary dysfunction.

The present invention also relates to:
- a pharmaceutical composition of the invention for use in the treatment of retinal degeneration related to ciliary dysfunction; preferably the pharmaceutical composition comprises an inhibitor of eIF2α, preferably guanabenz, and a compound increasing the expression and/or activity of protein BiP, preferably valproic acid, and optionally an inhibitor of caspase-12, preferably the peptide Ala-Thr-Ala-Asp(OMe)-fluoromethyl ketone (SEQ ID NO: 3);
- a pharmaceutical composition of the invention for use for preventing or reducing the endoplasmic reticulum stress induced by a ciliopathy;
- the use of an inhibitor of eIF2α, preferably guanabenz, and optionally a pharmaceutically acceptable carrier, for the manufacture of a medicament for the treatment of retinal degeneration related to ciliary dysfunction;
- the use of a compound increasing the expression and/or activity of protein BiP, preferably valproic acid, and optionally a pharmaceutically acceptable carrier, for the manufacture of a medicament for the treatment of retinal degeneration related to ciliary dysfunction;
- the use of an inhibitor of caspase-12, preferably the peptide Ala-Thr-Ala-Asp(OMe)-fluoromethyl ketone (SEQ ID NO: 3), and optionally a pharmaceutically acceptable carrier, for the manufacture of a medicament for the treatment of retinal degeneration related to ciliary dysfunction;
- the use of a combination of at least two compounds selected from the group consisting of an inhibitor of eIF2α, preferably guanabenz, a compound increasing the expression and/or activity of protein BiP, preferably valproic acid, and an inhibitor of caspase-12, preferably the peptide Ala-Thr-Ala-Asp(OMe)-fluoromethyl ketone (SEQ ID NO: 3), and optionally a pharmaceutically acceptable carrier, for the manufacture of a medicament for the treatment of retinal degeneration related to ciliary dysfunction;
- the use of an inhibitor of eIF2α, preferably guanabenz, and a compound increasing the expression and/or activity of protein BiP, preferably valproic acid, optionally an inhibitor of caspase-12, preferably the peptide Ala-Thr-Ala-Asp(OMe)-fluoromethyl ketone (SEQ ID NO: 3), and optionally a pharmaceutically acceptable carrier, for the manufacture of a medicament for the treatment of retinal degeneration related to ciliary dysfunction;
- the uses as described above for the manufacture of a medicament for preventing or reducing the endoplasmic reticulum stress induced by a ciliopathy;
- a product or kit containing at least two compounds selected from the group consisting of (a) an inhibitor of eIF2α, preferably guanabenz, (b) a compound increasing the expression and/or activity of protein BiP, preferably valproic acid, and (c) an inhibitor of caspase-12, preferably the peptide Ala-Thr-Ala-Asp(OMe)-fluoromethyl ketone (SEQ ID NO: 3), as a combined preparation for simultaneous, separate or sequential use, in particular in the treatment of retinal degeneration related to ciliary dysfunction;
- a product or kit containing (a) an inhibitor of eIF2α, preferably guanabenz, and (b) a compound increasing the expression and/or activity of protein BiP, preferably valproic acid, and optionally (c) an inhibitor of caspase-12, preferably the peptide Ala-Thr-Ala-Asp(OMe)-fluoromethyl ketone (SEQ ID NO: 3), as a combined preparation for simultaneous, separate or sequential use, in particular in the treatment of retinal degeneration related to ciliary dysfunction;
- a product or kit containing (a) an inhibitor of eIF2α, preferably guanabenz, (b) a compound increasing the expression and/or activity of protein BiP, preferably valproic acid, and (c) an inhibitor of caspase-12, preferably the peptide Ala-Thr-Ala-Asp(OMe)-fluoromethyl ketone (SEQ ID NO: 3), as a combined preparation for simultaneous, separate or sequential use, in particular in the treatment of retinal degeneration related to ciliary dysfunction;
- a product or kit as described above, as a combined preparation for simultaneous, separate or sequential use, in particular for preventing or reducing the endoplasmic reticulum stress induced by a ciliopathy;
- a method for treating retinal degeneration related to ciliary dysfunction, in a subject in need thereof, comprising administering a therapeutically efficient amount of a pharmaceutical composition of the invention; preferably, the pharmaceutical composition comprises an inhibitor of eIF2α, preferably guanabenz, and a compound increasing the expression and/or activity of protein BiP, preferably valproic acid, and optionally an inhibitor of caspase-12, preferably the peptide Ala-Thr-Ala-Asp(OMe)-fluoromethyl ketone (SEQ ID NO: 3);
- a method for preventing or reducing the endoplasmic reticulum stress induced by a ciliopathy, in a subject in need thereof, comprising administering a therapeutically efficient amount of a pharmaceutical composition of the invention; preferably, the pharmaceutical composition comprises an inhibitor of eIF2α, preferably guanabenz, and a compound increasing the expression and/or activity of protein BiP, preferably valproic acid, and optionally an inhibitor of caspase-12, preferably the peptide Ala-Thr-Ala-Asp(OMe)-fluoromethyl ketone (SEQ ID NO: 3);
- a method for treating retinal degeneration related to ciliary dysfunction, in a subject in need thereof, comprising administering a therapeutically efficient amount of a product or kit of the invention as described above; preferably the product or kit contains an inhibitor of eIF2α, preferably guanabenz, and a compound increasing the expression and/or activity of protein BiP, preferably valproic acid, and optionally an inhibitor of caspase-12, preferably the peptide Ala-Thr-Ala-Asp(OMe)-fluoromethyl ketone (SEQ ID NO: 3); and
- a method for preventing or reducing the endoplasmic reticulum stress induced by a ciliopathy, in a subject in need thereof, comprising administering a therapeutically efficient amount of a product or kit of the invention as described above; preferably the product or kit contains an inhibitor of eIF2α, preferably guanabenz, and a compound increasing the expression and/or activity of protein BiP, preferably valproic acid, and optionally an inhibitor of caspase-12, preferably the peptide Ala-Thr-Ala-Asp(OMe)-fluoromethyl ketone (SEQ ID NO: 3).

The pharmaceutical use according to the invention includes veterinary use.

The term "subject" refers to an animal, preferably to a mammal, even more preferably to a human, including an adult, a child and a human at the prenatal stage.

As used herein, the term "retinal degeneration related to ciliary dysfunction" refers to retinal degeneration induced by ciliopathy, i.e., primary cilium dysfunction and in particular photoreceptor-connecting cilium dysfunction. Ciliopathy can affect either a single organ (or tissue) or can lead to a full-blown syndromic spectrum of ciliopathy-related manifestations with various target organs involved simultaneously. Retinal degeneration related to ciliary dysfunction, in particular retinitis pigmentosa, may be isolated non-syndromic retinal degeneration due to mutations in specific retinal ciliary genes, or may be a feature of syndromic ciliopathy.

In particular, the retinal degeneration related to ciliary dysfunction may be induced by a ciliopathy selected from the group consisting of Bardet-Biedl syndrome, Senior-Loken syndrome, Mainzer-Saldino syndrome, Joubert syndrome, Jeune syndrome, Sensenbrenner syndrome, Meckel-Gruber syndrome, Alström syndrome, MORM syndrome, a subgroup of Leber's congenital amaurosis caused by mutation in a ciliary gene and X-linked retinitis pigmentosa caused by mutation in the RPGR gene.

These ciliopathies are caused by mutation in one or several genes involved in ciliary function. The mutation may induce a complete loss of function of the encoded protein or only a partial loss of function. The mutation may result in the creation of stop codons, frameshift mutations, amino acid substitutions, particular RNA splicing, processing or translation efficiency, product instability, truncated polypeptide production, etc. The mutation may result in the production of a polypeptide with altered function, stability, targeting or structure. It may also cause a reduction in protein expression that may be assessed for example by immunohistochemistry, semi-quantitative Western blot, or protein or antibody arrays.

Bardet-Biedl syndrome (OMIM: #209900) may be caused by mutation in the BBS1, BBS2, BBS3/ARL6, BBS4, BBS5, BBS6/MKKS, BBS7, BBS8, BBS9, BBS10, BBS11, BBS12, BBS13/MKS1, NPHP6/CEP290, BBS15/WDPCP, BBS16/SDCCAG8 or BBS17/LZTFL gene.

Senior-Loken syndrome (OMIM: #266900) may be caused by mutation in the NPHP6/CEP290, BBS16/SDCCAG8, NPHP1, NPHP2, NPHP3, NPHP4, NPHP5 or NPHP9/NEK8 gene.

Joubert syndrome (OMIM: #213300) may be caused by mutation in the NPHP6/CEP290, RPGRIP1L, CC2D2A, MKS3, INPP5E, AHI1, ARL13B, NPHP1 TMEM216, TMEM67, OFD1, TTC21B*, KIF7, TCTN1, TMEM237, CEP41, TMEM1138, C5orf42, TCTN3, ZNF423, TCTN2 or TMEM231 gene.

Mainzer-Saldino syndrome (OMIM #2666920) may be caused by mutation in the IFT140 gene.

Jeune syndrome, also named Jeune asphyxiating thoracic dystrophy (OMIM: #208500), may be caused by mutation in the IFT80, DYNC2H1, TTC21B or WDR19 gene.

Meckel-Gruber syndrome (OMIM: #249000) may be caused by mutation in the BBS13/MKS1, NPHP6/CEP290, BBS15/WDPCP, RPGRIP1L, CC2D2A, NPHP3, MKS2 or MKS3 gene.

Alström syndrome (OMIM: #203800) is caused by mutation in the ALMS1 gene.

MORM syndrome (mental retardation, truncal obesity, retinal dystrophy and micropenis) (OMIM: #610156) may be caused by mutation in the INPP5E gene.

Leber's congenital amaurosis (OMIM: #204000) is a heterogeneous very early onset retinal degeneration. A subset of genes identified to date are ciliary. In particular, the retinal degeneration related to ciliary dysfunction may be a ciliopathy belonging to a subgroup of Leber's congenital amaurosis caused by mutation in the NPHP6/CEP290, LCA5/Leberciline or RPGRIP1 gene.

The retinal degeneration related to ciliary dysfunction may also be an X-linked retinitis pigmentosa (OMIM: #300029) caused by mutation in the RPGR gene.

Sensenbrenner syndrome (OMIM #218330) may be caused by mutation in the WDR19, WDR35, IFT122 or IFT43 gene.

Thus, the retinal degeneration related to ciliary dysfunction may be induced by a ciliopathy caused by a mutation in a gene selected from the group consisting of BBS1, BBS2, BBS3/ARL6, BBS4, BBS5, BBS6/MKKS, BBS7, BBS8, BBS9, BBS10, BBS11, BBS12, BBS13/MKS1, NPHP6/CEP290, BBS15/WDPCP, BBS16/SDCCAG8, BBS17/LZTFL1, RPGRIP1L, CC2D2A, NPHP3, MKS2, MKS3, INPP5E, AHI1, ARL13B, NPHP1, NPHP2, NPHP3, NPHP4, NPHP5, NPHP9/NEK8, TMEM216, TMEM167, OFD1, TTC21B*, KIF7, TCTN1, TMEM237, CEP41, TMEM1138, C5orf42, TCTN3, ZNF423, TCTN2, TMEM231, IFT140, IFT80, DYNC2H1, TTC21B, WDR19, WDR35, IFT122, IFT43, ALMS1, LCA5 and RPGR.

In a particular embodiment, the retinal degeneration is induced by Bardet-Biedl syndrome.

As used herein, the term "treatment", "treat" or "treating" refers to any act intended to ameliorate the health status of patients, such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

In particular, the term "treatment of retinal degeneration related to ciliary dysfunction" may refer to a preservation or an improvement of the light-detecting capacity of the photoreceptors, in particular with an increased magnitude of the a-wave on electroretinogram recordings. This term may also refer to a reduction of the apoptosis of photoreceptors in the retina and/or a increase of the thickness of the outer nuclear layer.

The term "therapeutically efficient amount" refers to an amount of an inhibitor of eIF2α, a compound increasing the expression and/or activity of protein BiP, and/or an inhibitor of caspase-12 administered to a subject that is sufficient to constitute a treatment as defined above of retinal degeneration related to ciliary dysfunction.

In the method for treating retinal degeneration related to ciliary dysfunction of the invention, the pharmaceutical composition or the product or kit may be administered using any suitable route, in particular topically, orally, intradermally, parenterally and/or intraocularly, preferably intraocularly.

The method of the invention may also further comprise administering at least one additional therapeutic agent to the subject. In particular, said therapeutic agent may be selected from the group consisting of a chemotherapeutic agent, a corticosteroid, an antibiotic, an analgesic, an alpha-adrenergic blocker, an alpha-adrenergic agonist, a beta-adrenergic agonist, an anticholinergic, an inhibitor of 5-alpha-reductase, an androgen, an immunomodulator, an immunosuppressant, an anti-angiogenic such as anti-VEGF, anti-FGF, anti-HGF and anti-EFG, a leukotriene modifier, an aminosalicylate, an anesthetic, a non-steroidal anti-inflammatory, an antiparasitic, a therapy of the solubilized interleukin receptor, a cytotoxin, an antioxidant, and any combinations thereof.

Although these drugs, i.e., the inhibitor of eIF2α, the compound increasing the expression and/or activity of protein BiP and the inhibitor of caspase-12, have shown some effects when tested separately, the combination of the two or three molecules has proven to be far more effective in preventing apoptosis. Remarkably, the combination of these drugs has also allowed the inventors to reduce the doses administered to the in vivo models, limiting to the maximum any possible side effects.

This potentiating effect allows to use decreased amounts of the inhibitor of eIF2α, the compound increasing the expression and/or activity of protein BiP and/or the inhibitor of caspase-12. Thus, with the pharmaceutical composition, combination, product, kit or combined treatment of the invention, it is possible to preserve, or even improve, the efficacy of the treatment, while reducing adverse or toxic effects.

Thus, in an embodiment, at least two compounds selected from the group consisting of an inhibitor of eIF2α, preferably guanabenz, an compound increasing the expression and/or activity of protein BiP, preferably valproic acid, and an inhibitor of caspase-12, preferably the peptide Ala-Thr-Ala-Asp(OMe)-fluoromethyl ketone (SEQ ID NO: 3), are present in the pharmaceutical composition, product or kit, or are administered to the subject in need thereof at subtherapeutic doses.

In a particular embodiment, an inhibitor of eIF2α, preferably guanabenz, and an compound increasing the expression and/or activity of protein BiP, preferably valproic acid, and optionally an inhibitor of caspase-12, preferably the peptide Ala-Thr-Ala-Asp(OMe)-fluoromethyl ketone (SEQ ID NO: 3), are present in the pharmaceutical composition, product or kit, or are administered to the subject in need thereof at subtherapeutic doses.

In particular, the pharmaceutical composition, product or kit comprises an inhibitor of eIF2α, preferably guanabenz, and an compound increasing the expression and/or activity of protein BiP, preferably valproic acid, and the relative amounts of the inhibitor of eIF2α and the compound increasing the expression and/or activity of protein BiP are such that they exhibit a synergistic therapeutic effect upon administration to a subject, preferably one or both being used at subtherapeutic dose.

As used herein, the term "subtherapeutic dose" refers to an amount or dose of a therapeutic agent lower than the conventional dose administered to a subject for the same indication and the same administration route when it is used alone. In particular, it refers to an amount or dose of a therapeutic agent which has no or only a slight effect when used alone. In particular, the subtherapeutic dose may be 90, 80, 70, 60, 50, 40, 30, 20 or 10% of the conventional dose.

Alternatively, instead of lowering the amount or dosage of compounds, the administration frequency or the treatment period may be reduced.

EXEMPLARY ASPECTS OF THE INVENTION

1. A pharmaceutical composition comprising an inhibitor of eIF2α and/or an inhibitor of CASPASE 12 and/or a compound increasing the expression and/or activity of protein BiP.

2. The pharmaceutical composition of aspect 1, comprising at least two compounds selected from the group consisting of an inhibitor of eIF2α, an inhibitor of CASPASE 12, and a compound increasing the expression and/or activity of protein BiP.

3. The pharmaceutical composition of aspect 1 or 2, comprising an inhibitor of eIF2α, an inhibitor of CASPASE 12 and a compound increasing the expression and/or activity of protein BiP.

4. A composition according to any one of aspects 1 to 3, wherein the inhibitor of eIf2-α is GBZ.

5. A composition according to any one of aspects 1 to 4, wherein the inhibitor of Caspase 12 is a peptide targeting the catalytical site of the CASPASE 12 enzyme, preferably a peptide of formula Ala-Thr-Ala-Asp(OMe)-fluoromethyl ketone (SEQ ID NO: 3).

6. A composition according to any one of aspects 1 to 5, wherein the compound increasing the expression and/or activity of protein BiP is VPA.

7. A composition according to any one of aspects 1 to 6, comprising the combination of GBZ, a peptide of formula Ala-Thr-Ala-Asp(OMe)-fluoromethyl ketone (SEQ ID NO: 3) and VPA.

8. The composition according to any one of aspects 1-6 for preventing or reducing the endoplasmic reticulum stress induced by a ciliopathy.

9. The composition according to any one of aspects 1-7 for use in the treatment of retinal degeneration, in particular retinal degeneration related to ciliary dysfunction.

10. The composition of aspect 8, wherein the retinal degeneration is induced by Bardet-Biedl syndrome.

11. A pharmaceutical composition comprising an inhibitor of eIF2α and/or an inhibitor of CASPASE 12 to be used in combination with a compound increasing the expression and/or activity of protein BiP.

12. A product containing at least two compounds selected from the group consisting of an inhibitor of eIF2α, preferably GBZ, an inhibitor of CASPASE 12, preferably the peptide Ala-Thr-Ala-Asp(OMe)-fluoromethyl ketone (SEQ ID NO: 3), and a compound increasing the expression and/or activity of protein BiP, preferably VPA, as a combined preparation for simultaneous, separate or sequential use in the treatment of retinal ciliopathy or retinal degeneration.

13. The product of aspect 12 containing an inhibitor of eIF2α, preferably GBZ, an inhibitor of CASPASE 12, preferably the peptide Ala-Thr-Ala-Asp(OMe)-fluoromethyl ketone (SEQ ID NO: 3), and a compound increasing the expression and/or activity of protein BiP, preferably VPA.

14. A method for treating or preventing retinal degeneration in a subject, said method comprising the step consisting of administering a therapeutically effective amount of a pharmaceutical composition as defined in any one of aspects 1 to 11 or a product of aspect 12 or 13 to the subject in need thereof.

15. The method according to aspect 14, wherein the pharmaceutical composition or the product is administered topically, orally, intradermally, parenterally and/or intraocularly.

16. The method according to aspect 14 or 15, further comprising administering at least one additional therapeutic agent to the subject.

17. The method according to aspect 16, wherein said at least one additional therapeutic agent is selected from the group consisting of a chemotherapeutic agent, a corticosteroid, an antibiotic, an analgesic, an alpha-adrenergic blocker, an alpha-adrenergic agonist, a beta-adrenergic agonist, an anticholinergic, an inhibitor of 5-alpha-reductase, an androgen, an immunomodulator, an immunosuppressant, an anti-angiogenic such as anti-VEGF, anti-FGF, anti-HGF and anti-EFG, a leukotriene modifier, an aminosalicylate, an anesthetic, a non-steroidal anti-inflammatory, an antiparasitic, a therapy of the solubilized interleukin receptor, a cytotoxin, an antioxidant, and any combinations thereof.

All patents, patent applications, provisional applications, and publications referred to or cited herein are incorporated by reference in their entirety, including all figures and tables, to the extent they are not inconsistent with the explicit teachings of this specification.

The following examples are given for purposes of illustration and not by way of limitation.

EXAMPLES

Materials and Methods

Retinal Explants

Wild-type animals were on a C57BL/6 background. The retinal explant culture procedure was carried out as previously described (Reidel et al., 2006). Briefly, 15-day-old mice were sacrificed by decapitation and eyes were removed and incubated in trypsin (catalog #25200-072, Gibco, Invitrogen, Paris, France) for 10 min at 37° C. Digestion was stopped by transferring eyes in DMEM+10% fetal bovine serum (catalog #31885-023 and 10500-064, Gibco) and incubation for 10 min at 4° C. Eyes were dissected in Ame's medium (catalog#15230-097, Gibco) supplemented with 6.5 g/L glucose. First, the sclera was carefully removed, leaving the retinal pigmented epithelium (RPE) attached to the eyeball. Incisions were made at the edge of the cornea to remove the cornea, lens and hyaloid body. Then four radial incisions were made in the retina to obtain a cross shape. Retinas were transferred on a nitrocellulose culture membrane (catalog # PICMORG50, Millipore, Molsheim, France) with RPE side down and cultivated in Neurobasal A medium (catalog #108888-022, Gibco) supplemented with B27 supplement (catalog #17504-044, Gibco), L-glutamine (catalog #35050-061, Gibco) and penicillin/streptomycin (catalog #15240; Gibco). Explants were maintained at 37° C. humidified 5% $CO_2$. Specific gene silencing using lentiviruses carrying shRNA sequences for Bbs12, Perk, Hri or Rhodopsin (Santa Cruz Biotechnology, Tebu Bio, Yvelines, France) were performed by adding 20 µl of viral suspension ($1 \times 10^5$ infectious units) in the culture medium overnight before whole medium change. The infected explants were then cultured for 3 days with a half medium change on a daily basis. Explants were not maintained longer in culture to avoid unspecific apoptosis in the different retinal layers. For pharmacological treatments, 2 mM valproic acid (VPA dissolved in ethanol 100%; catalogue number 4543; Sigma-Aldrich), 25 µM guanabenz (GBZ dissolved in $Me_2SO$; catalogue number 0889; Tocris Bioscience, Ellisville, Mo.), or 10 µM caspase-12 inhibitor (named INH dissolved in $Me_2SO$, the synthetic peptide Z-Ala-Thr-Ala-Asp(O-methyl)-fluoromethyl-ketone (SEQ ID NO: 3); catalogue number PK-CA577-1079-100; Promokine, Heidelberg, Germany) were added for single treatments and at a 10-fold dilution for combined treatments: GIV (GBZ 2.5 µM+1 µM INH+0.2 mM VPA) or GV (2.5 µM GBZ+0.2 mM VPA). Drugs were added simultaneously with viral infection to the culture medium.

For immunofluorescence experiments and TUNEL assay retinal explants were fixed directly on membranes with Formalin 10% for 1 hour at 4° C. Sucrose impregnation was then performed using 10%, 20% and 30% sucrose baths, 20 min each. Explants were transferred to OCT (catalog #4583, Tissue-Tek, Sakura, Villeneuve d'Ascq, France) in mold and frozen in liquid nitrogen. 8 µm thin cryosections were mounted on StarFrost slides (catalog # VS1117, Waldemar Knittel Glasbearbeitungs, Braunschweig, Germany).

Light Adaptation Experiments

Light adaptation experiments were carried at 37° C. on explants after 3 days of culture to allow gene knock-down. For dark to light experiments, explants were dark-adapted for 4 hours and then exposed to 200 lux for 30 minutes by light-emitting diodes. For light to dark condition, explants were exposed to 200 lux for 15 minutes before dark adaptation for 45 minutes. After treatment, the explants were fixed with 4% formaldehyde in the illumination condition used.

$Bbs12^{-/-}$ Mice Breeding and Pharmacological Treatments

The $Bbs12^{-/-}$ mice were generated as previously described. $Bbs12^{-/-}$ mice were obtained by crossing heterozygote animals. Mice were housed in humidity and temperature controlled rooms on a 12-hour light/12-hour dark cycle with food ad libitum and water. For anti-apoptotic treatments, animals were treated with eye drops from 2 to 4 weeks of age once a day; the eye drops contain GBZ 7.5 µM and Caspase Inhibitor 500 µM for the left eye and contain 5% DMSO for the right eye. From 3 to 4 weeks of age, after weaning, VPA or GBZ were added in the drinking water at concentrations of 5 mg/mL and 50 µM, respectively. Eye drop treatment was achieved from 2 to 4 weeks of age and systemic treatments were achieved from 3 to 4 weeks of age. At 4 weeks of age, electrophysiological analyses were performed and the retinas were harvested for molecular analysis.

Electroretinogram Analysis

Mice were dark adapted for 12 hours before recording. Those experiments were performed under dim red light. The mice were anesthetized with the same anesthesia mix described in the section above. The pupils were dilated with eye drops of atropine 0.3% (catalog # Atropine Alcon 0.3%, Alcon, Rueil-Malmaison, France). Animals were placed on a controlled heating pad and maintained at 37° C. during the procedure. The reference electrode was placed under the head skin and the background electrode was inserted in the tail of the animal. The measuring electrode was placed on the cornea, to optimize contact between the cornea and the gold electrode, and a drop of methylcellulose gel (catalog # Ocry-gel, TVM Laboratories, Lempdes, France) was added. Flashes were delivered though a Ganzfeld equipped with light-emitting diodes with maximum output of 318 $cd/m^2$ (Siem Biomédicale, Nimes, France). For the scotopic ERG, the flash duration varied from 3 to 5 ms with final flash output ranging from 0.001 to 1 $cd*s/m^2$. Responses were amplified, filtered (1-300-Hz band pass), and digitized (Visiosystem; Siem Biomédicale). The a and b waves were measured by using a 1-75-Hz band pass to filter oscillatory potentials.

RNA Extraction and Quantitative PCR

Total RNA was extracted with Trizol (catalog #15596-018, Invitrogen). One of total RNA was DNAse treated using TURBO DNA-free Kit (catalog # AM1907, Applied Biosystems, Villebon-sur-Yvette, France) and then reverse transcribed using the iScript cDNA synthesis kit (catalog #170-8891, BioRad, Marne-la-coquette, France). Primers (listed in supplementary methods) were purchased from Qiagen, Courtaboeuf, France. Quantitative PCR were performed using SYBR Green PCR Mix (catalog #4367659, Applied Biosystems) on a BioRad CFX96 system. mRNA expressions were expressed as relative to Gapdh RNA content, using BioRad CFX manager software. For endoplasmic reticulum stress arrays, Custom TaqMan Array 96 was purchased for Applied Biosystems; all tested genes are listed in supplementary methods.

RT-PCR Analysis of Xbp1 Splicing

RNAs were extracted and reverse transcribed as described above. cDNAs were used for PCR amplification of both unspliced and spliced variants of Xbp1 using primers: 5'-TTACGGGAGAAAACTCACGGC-3' (SEQ ID NO: 1) and 5'-GGGTCCAACTTGTCCAGAATGC-3' (SEQ ID NO: 2) (Lin et al., 2007). PCR was done using RedTaq DNA polymerase (catalog # D4309-50UN, Sigma-Aldrich) using the cycling: 95° C. for 5 min—[95° C. for 1 min—58° C. for 30 sec—72° C. for 30 sec] 35 cycles—72° C. for 5 min.

Western Blots, Immunofluorescence Microscopy and TUNEL Assay

Proteins were obtained by lysis in RIPA buffer (150 mM NaCl, 50 mM TrisHCl pH 8, 0.1% Tween20, catalog # P7653, T3253, 93773, Sigma-Aldrich) supplemented with Protease Inhibitors Complete Mini EDTA-free (catalog #11836 170001, Roche, Boullogne-Billancourt, France), 1 mM $NaVO_4$ and 25 mM NaF (catalog # S6508 and S7920, Sigma-Aldrich). After retina dissociation using dounce homogenizer, samples were sonicated and protein concentration was determined using Bradford reagent (catalog #500-0006, BioRad). For Western blotting, 80 μg of whole protein extracts were loaded per lane and Ponceau S staining was used as loading control for signal quantification. Antibody binding was visualized using SuperSignal West Femto Maximum Sensitivity Substrate (catalog #34095, Thermo-Fisher) on a Versadoc apparitus, BioRad. Signal quantification was assed using QuantityOne software from BioRad.

Sections or cells were washed with PBS 1× and shortly fixed with Formalin 10% solution for 5 minutes and washed three times with PBS 1×. The sections were then pre-incubated with Teng-T (10 mM TrisHCl (pH=7.6), 5 mM EDTA (catalog # E5768, Sigma-Aldrich), 150 mM NaCl, 0.25% gelatin (catalog # G9391, Sigma-Aldrich), 0.05% Tween-20)/10% normal goat serum (catalog #PCN5000, Gibco) for 30 min, followed by an overnight incubation with the primary antibody diluted in Teng-T/10% NGS at 4° C. Slides were then washed with PBS 1× and incubated with the indicated secondary antibody in Teng-T/10% NGS for 1 hour at room temperature. Slides were washed in PBS 1× and nuclear staining was performed with DAPI (catalog # D1306, Invitrogen). Slides were mounted with Immumount (catalog #9990402, ThermoFisher). TUNEL assays were performed using In Situ Cell Death Detection Kit (catalog #11684795910, Roche) according to suppliers' protocol. The prevalence of apoptotic nuclei was expressed as the ratio of TUNEL-positive nuclei and DAPI-stained nuclei in three different areas of the ONL per experiment. All results shown are representative of at least 3 separate experiments.

Transmission Electron Microscopy

Samples were fixed in Karnovsky fixative and postfixed within 0.1 M cacodylate buffer containing 1% weight by volume osmium tetroxide for 1 h at 4° C. Samples were then dehydrated through graded alcohol and embedded in Epon 812 resin. Ultrathin sections of 70 nm were cut and contrasted with uranyl acetate and lead citrate. Pictures of the sections were made using a Philips Morgagni 268D transmission electron microscope.

Antibodies

Primary antibodies used: Rabbit polyclonal anti-BBS10 (catalog #12421, ProteinTech), mouse polyclonal anti-BBS12 (catalog # H00166369-Bo1P, Abnova, Colmar, France), mouse monoclonal anti-Rhodopsin Rho-4D2 (Hicks et al., 1986), rabbit monoclonal anti-cleaved-PARP, mouse monoclonal anti-eIF2alpha, rabbit monoclonal anti-Phospho-eIF2alpha, rabbit monoclonal anti-BIP, mouse monoclonal anti-CHOP10, (catalog #9544, #2103, #3597, #3177, #2895 respectively, all purchased from Cell Signaling, Ozyme, Saint-Quentin-Yveline, France), mouse monoclonal anti-O-Tubulin (catalog # TUB-2A2, Euromedex, Souffeliweyersheim, France), mouse monoclonal anti-β-Tubulin (catalog # ab11316-100, Abcam, Paris, France), and mouse monoclonal anti-acetylated-β-Tubulin (catalog #32-2700 Zymed Laboratories, Invitrogen). Different secondary antibodies were used for immunofluorescence experiments: goat anti-mouse FITC (catalog #81-6511, Zymed Laboratories), donkey anti-rabbit Texas Red (catalog # ab6800, Abcam), and anti-mouse Alexa 594, anti-rabbit FITC, donkey anti-goat IG-TR (catalog # sc-2783, Santa Cruz), donkey anti-rabbit Ig-FITC (catalog # sc-2090, Santa Cruz), rabbit anti-mouse Alexa 488, and goat anti-mouse Fluor 594 (catalog # A-11059 and A-10032, Molecular Probes, Invitrogen).

Toxicological Analysis

For treatments, the mice were fed ad libitum for a 10-week period with water supplemented with either VPA 5 mg/ml or GBZ 50 μM or DMSO 0.003% as control.

After 10 weeks of treatment, rate of urea synthesis was measured as published in Hallemeesch et al., 2001. Briefly, animals were anesthetized with a 25 μl/10 grams of body weight anesthesia mix (100 ml Domitor (catalog # Domitor 1 mg/ml, Janssen-Cilag, Issy-les-Moulineaux, France)+314 ml Ketamine (catalog # Ketamine 1000, Virbac, Carros, France)+4 ml 0.9% NaCl solution). The mice were placed on a controlled heating pad and maintained at 37° C. during the procedure. An intrajugular catheter was fixed to infuse a labeled urea solution at the initial rate of 4 ml/h for 7 minutes and 0.5 ml/h for the next 2 hours. The solution is 0.9% NaCl supplemented with 24 μmol $NaHCO_3$ (catalog # S5761, Sigma-Aldrich) and 3.6 μmol labeled urea (catalog # COLM-4861-0.5, Cambridge Isotope Laboratories, Andover, USA) per 10 grams of body weight. After 2 hours of perfusion, blood was sampled from the caveal vein caudal to the kidney. Blood samples were centrifuged at 12,000 g for 12 minutes and 80 μl of plasma was precipitated with 6.4 mg of sulfo-salicylic acid (catalog # S7422, Sigma-Aldrich) for further analysis of urea enrichment and amino acid concentration. Plasma amino acid concentrations were measured by gradient reversed phase high performance liquid chromatography with precolumn derivation with o-phatalaldehyde (Pierce) and 3-mercaptopropionic acid (Sigma-Aldrich), Omnisphere 3 C18 column (Varian) and fluorescent detection (Van Eijk et al., 1993). Plasma urea concentrations were determined using the colorimetric method using the Sigma complete reagent kit blood urea nitrogen test, according to manufacturer instructions with absorbance measurements at 540 nm. Tracers were measured by analyzing 25 ul plasma using tandem liquid chromatography mass spectrometry. Enrichment is given as the tracer-tracee ratio, corrected for the natural abundance of the stable isotope. Detection was based on parent fragmentation—ionization and daughter detection on mass and charge.

Following are examples which illustrate procedures for practicing the invention. These examples should not be construed as limiting. All percentages are by weight and all solvent mixture proportions are by volume unless otherwise noted.

Results

Bbs12 Depletion in Retinal Explants Leads to Photoreceptor Dysmorphy

Figure 7:
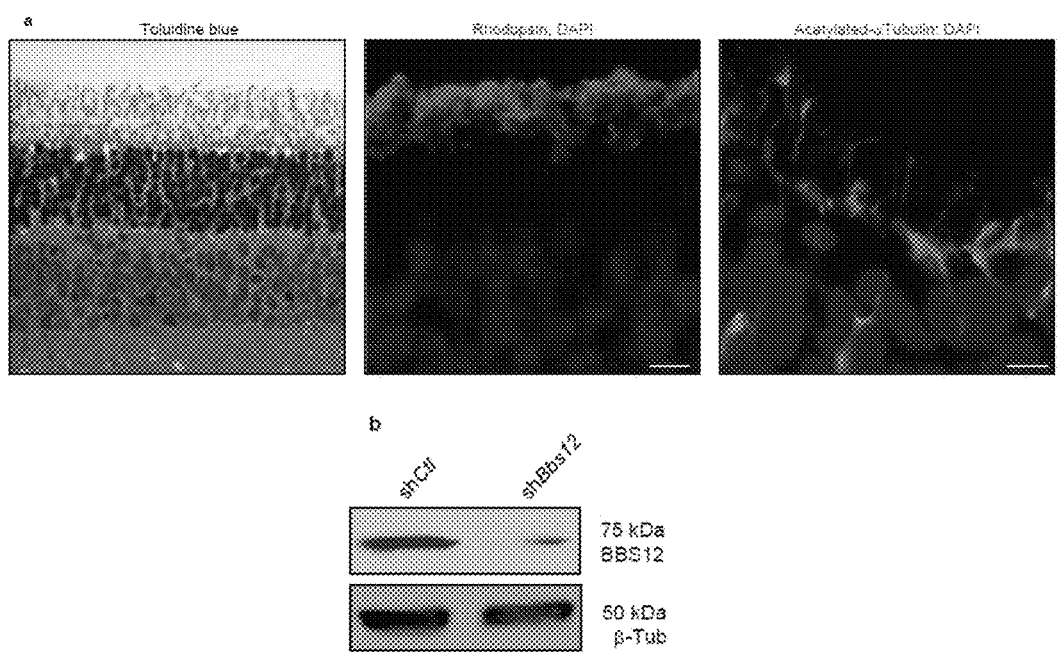
FIG. 7 Photoreceptor integrity in retinal explant cultures. (a) Toluidine blue staining (left panel), immunostaining of Rhodopsin with DAPI co-staining (middle panel), immunostaining of acetylated-αTubulin (right panel) with DAPI co-staining in retinal explants sections cultured for 4 days. (b) BBS12 and βTubulin as loading control proteins level in shCtl and shBbs12 treated explants. Scale bars 5 μm.

To investigate the involvement of ER stress in the mechanisms of photoreceptor cell death in BBS, we established an ex-vivo model using retinal explant cultures maintaining retinal organization and photoreceptor compartmentalization (FIG. 7). Upon shRNA-mediated Bbs12 depletion, expression levels of Bbs12 RNA were reduced by 40% (FIG. 1a) resulting in a significant decrease in BBS12 protein level (FIG. 1b). This depletion induced general disorganization of the photoreceptors' ONL and OS which was associated with a drastic reduction of CC and disk dilatation in OS (FIGS. 1c and 1d). ICT in the BBS12-deprived photoreceptor was defective as exemplified by the accumulation of Rhodopsin in the ONL (FIG. 1e). This loss of ICT was not Rhodopsin specific as dark-light experiments to assess the ICT of Arrestin revealed an absence of relocalization toward the OS upon photonic stimulation (FIG. 10.

Figure 2:
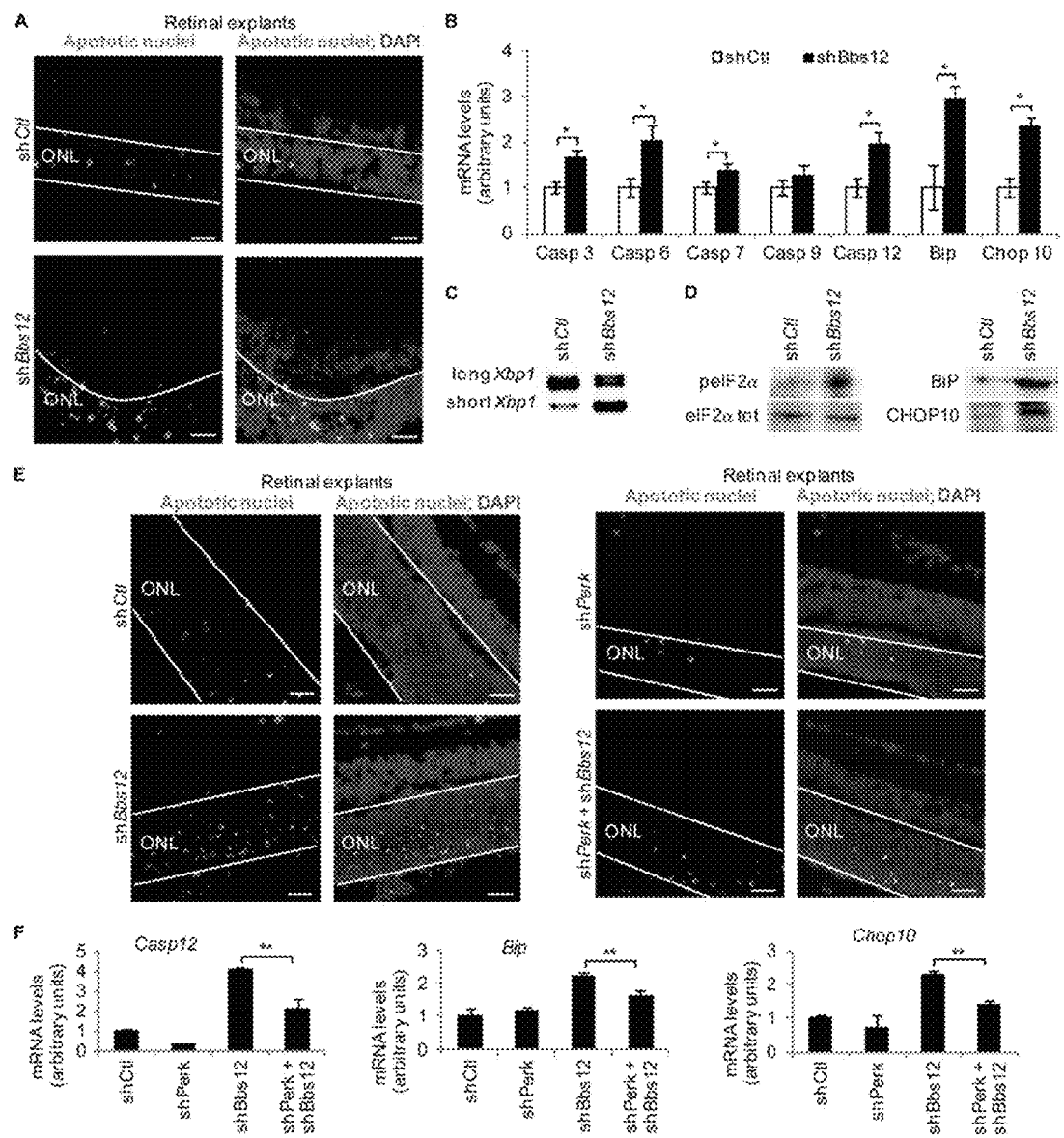
FIG. 2 Bbs12 depleted explants present ER stress. (a) TUNEL assays of shCtl and shBbs12 treated explants. 72 h after infection; apoptotic nuclei labeled in green and DAPI counterstaining. Scale bars, 25 μm. See FIG. 8 for corresponding apoptotic levels. (b) Expression analysis of caspase-3, -6, -7, -9, -12, Bip and Chop10 in shCtl and shBbs12 treated explants (n=3). *P<0.01. (c) RT-PCR of both long (unstressed) and short (unfolded protein response-related) isoforms of Xbp1. (d) Western blot analysis of phosphorylated and total eIF2α contents, CHOP10 and BiP in the indicated shRNA-treated explants. See FIG. 8 for loading controls and quantification. (e) TUNEL assays in shCtl, shBbs12, shPerk, or shBbs12+ shPerk-treated explants. Scale bars, 25 μm. See FIG. 8 for corresponding apoptotic levels and Perk knockdown validation. (f) Expression analysis of caspase-12, Bip and Chop10 in shBbs12 and shPerk treated explants. Scale bars 25 **P<0.05.
Figure 8:
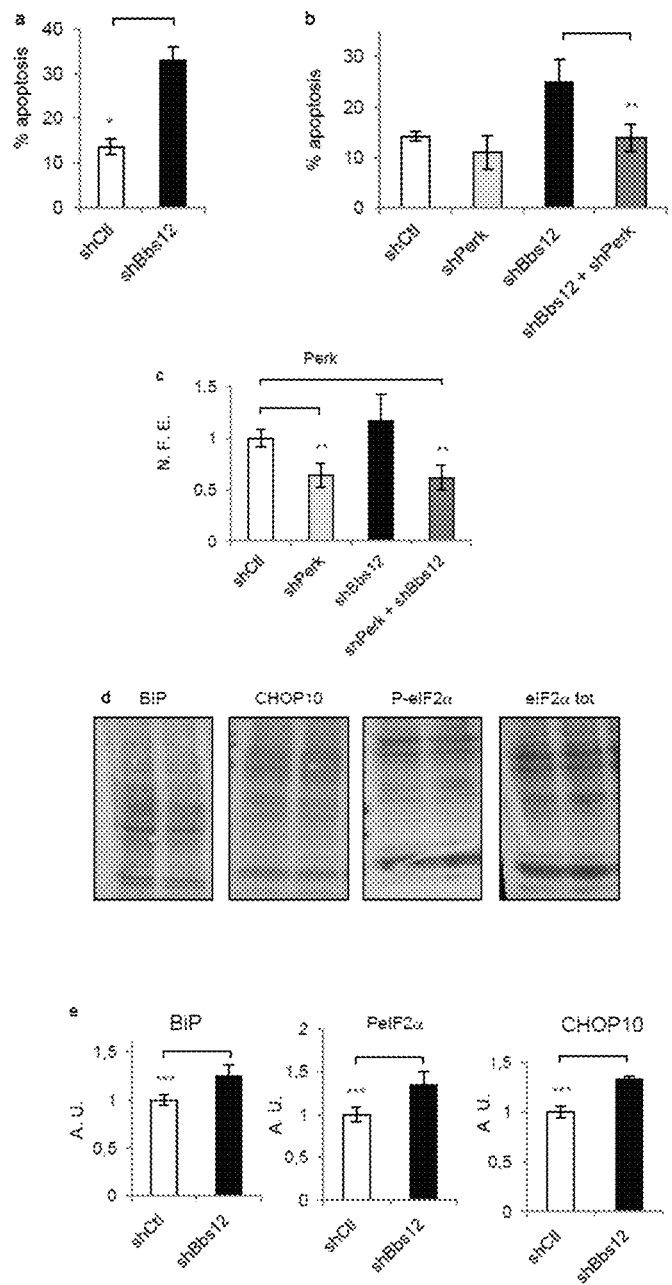
FIG. 8 Bbs12 depleted explants present ER stress mediated by PERK. (a) Apoptotic rate in shCtl and shBbs12 treated explants (n=3). *P<0.001. (b-c) Synergic depletion of Bbs12 and Perk in retinal explants: (b) Apoptotic rate (n=3). P<0.02. (c) Perk mRNA expression (n=3). P<0.05. (d) Ponceau staining as loading control for Western blots of shCtl and shBbs12 treated explants. (e) Corresponding protein quantification (calculated as intensity of immunoblotting signal/intensity of Ponceau staining, n=3). ***P<0.05.

PERK-in Bbs12 Knockdown in Retinal Explants Induces ER-Stress Mediated Photoreceptor Cell Death To assess the extent of the photoreceptor cell death after Bbs12 inactivation, we performed TUNEL assays and found 3-fold more apoptotic cells in shBbs12-treated retinal explants (FIG. 2a and FIG. 8). As caspases have a central role in programmed cell death execution, their expression was assessed (FIG. 2b). Effector Caspase3, 6 and 7 RNA were all up-regulated. Caspase9 mRNA level, linked to a mitochondrial defect, remained unchanged whereas Caspase12 mRNA level, associated to ER stress, was increased twofold in Bbs12 depleted explants. Subsequent analysis of specific ER stress genes like Bip and Chop10 exhibited a concomitant upregulation in the absence of BBS12 (FIG. 2b). We performed RT-PCR of both long and short isoforms of Xbp1 and the short isoform was more abundant in shBbs12 treated explants (FIG. 2c). At the protein level, BiP and CHOP10 were both 50% increased. Phosphorylation status of eIF2α was increased after Bbs12 depletion (FIG. 2d and FIG. 8). To test the eIF2α kinase involved in ER stress, we performed Perk knock down. Perk mRNA depletion alone (40% of mRNA decrease, FIG. 8c) did not affect Caspase12, Chop10 and Bip expression levels (FIG. 2f). On the other hand, synergic depletion of Perk and Bbs12 reduced Caspase12, Chop10, and Bip mRNA level expressions compared to shBbs12 alone which translated to a clear reduction of apoptotic nuclei in the photoreceptors (FIG. 2e; see FIG. 9b for quantification).

Figure 3:
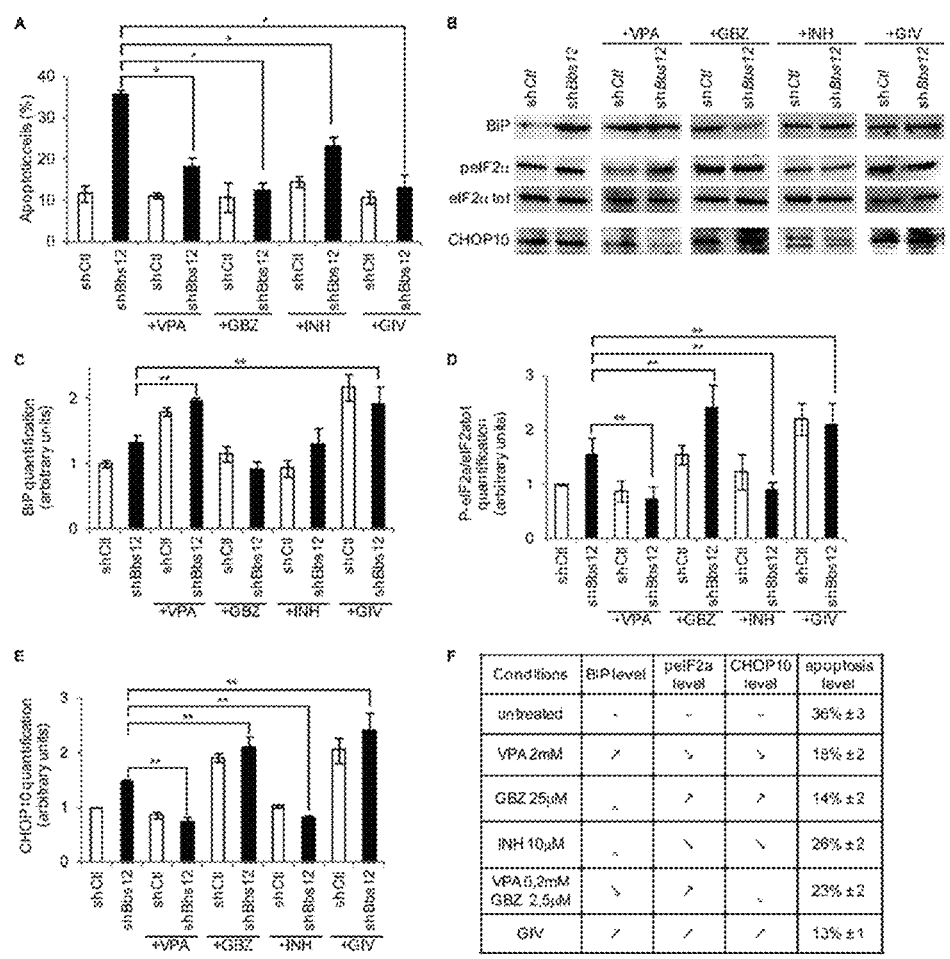
FIG. 3 Pharmacological treatments reduce ER stress in Bbs12 depleted explants. (a) Effect on apoptotic levels of VPA, GBZ, INH or GIV treatments on shCtl and shBbs12 explants (counted as TUNEL positive nuclei/DAPI in the ONL, n=3). *, p<0.01. (b) Immunodetection of peIF2α, eIF2αtot, CHOP10, and BiP in the indicated shRNA-treated explants. (c-e) Quantification of peIF2α/tot, CHOP10, and BiP levels in the indicated shRNA-treated explants (n=3). **,p<0.05. (f) Table summarizing the effect of the different treatments on targeted proteins and apoptosis level (%_S.E.). See FIG. 16 for VPA 0.2 mM_GBZ 2.5 μM treated explants.
Figure 4:
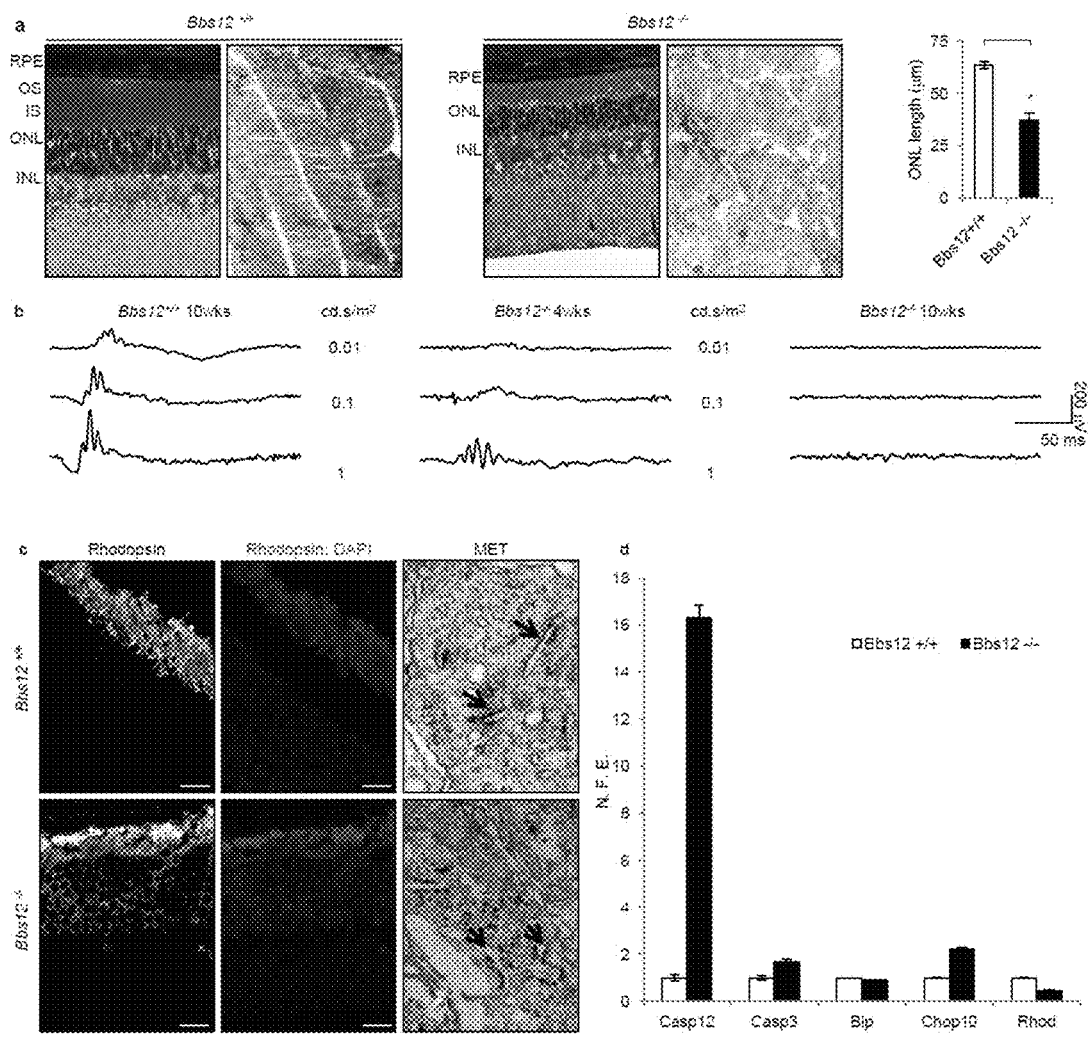
FIG. 4 Bbs12$^{-/-}$ mouse has retinal degeneration. (a) Toluidine blue stained sections of the Bbs12$^{+/+}$ (left panel) and Bbs12$^{-/-}$ (right panel) retinas and MET pictures of the OS; graph represents measurements of the ONL thickness of the Bbs12$^{+/+}$ and Bbs12$^{-/-}$ mice at 4 weeks of age (n=6). *P<0.002 (b) Representative scotopic ERG recording of the 10-week-old Bbs12$^{+/\pm}$ (left panel) and Bbs12$^{-/-}$ mice at 4 weeks of age (middle panel) and 10 weeks of age (right panel). (c) Immunostaining of Rhodopsin with and without DAPI co-staining in Bbs12$^{+/+}$ and Bbs12$^{-/-}$ retinas, MET analysis of IS in both genotypes with ER cisternae encircled in red (right panel). (d) Expression analysis of Caspase3, -6, -7, -12, Bip and Chop10 in Bbs12$^{+/+}$ and Bbs12$^{-/-}$ retinas (n=3). Scale bars 20 μm.

ER-Stress Induced Apoptosis of the Photoreceptors is Alleviated by Targeted Pharmacological Treatments We tested pharmacological treatments to reduce ER stress. Based on our findings, BiP, PERK-mediated phosphorylation of eIF2α and Caspase12 are key UPR actors in Bbs12-deprived photoreceptor phenotype. First, we tested valproic acid (VPA), known to modulate BiP transcription and activity. shCtl+VPA treated retinas presented an unchanged apoptotic rate of 13% whereas shBbs12+VPA treated explants had a significant lower apoptotic rate: 17% compared to the non-VPA treated explants (FIG. 3a and FIG. 10a). We analyzed mRNA expression of ER stress related genes (FIG. 4b). In control conditions, VPA treatment induced a twofold increase of Bip expression whereas Chop10 and Caspase12 mRNA were both not significantly changed. After Bbs12 depletion, VPA treatment induced a lower Bip, Chop10 and Caspase12 mRNA expression. At the protein level, VPA treatment decreased eIF2α phosphorylation and CHOP10 protein content and increased BiP (FIG. 4c and FIGS. 11a and 11b).

We also tested guanabenz (GBZ), an inhibitor of Growth Arrest and DNA Damage-inducible protein (GADD34), the eIF2α phosphatase (Tsaytler et al., 2011). It significantly reduces the proportion of apoptotic photoreceptor nucleus after Bbs12 depletion from 33% without treatment to 12% with GBZ (FIG. 3a). Tested stress gene expression (Caspase12, Chop10 and Bip) were also decreased with the treatment (FIG. 3). Moreover, GBZ treatment allowed eIF2α to be maintained in a phosphorylated status and induced an increase of CHOP10 but not BiP (FIG. 3 and FIGS. 11c and 11d).

We chose to also test a synthetic peptide designed to specifically inactivate Caspase12 activity named INH. INH decreased the apoptotic rate to 23% in shBbs12+INH explants (FIG. 3a). The inactivation of Caspase12 being achieved by its irreversible linkage with the peptide, we did not assess gene or protein expression analysis in these conditions.

As GBZ, VPA and INH were complementary in their actions, we combined them, with respective concentrations of 2.5 µM, 0.2 µM and 1 in a single pharmacological treatment termed GIV and treated the explants. It clearly appeared that the combination of the three drugs allowed reduction of the apoptotic photoreceptor rate to the control level as assessed by TUNEL assays (FIG. 3).

The combination of VPA, GBZ, and INH in the GIV treatment was more efficient at decreasing apoptosis than any of the individual components of this combination at a 10-fold higher concentration. Indeed, the impact of Bbs12 inactivation was completely balanced by the simultaneous pharmacological modulation of all three targets. The impact of INH on apoptosis correlated with a decrease in peIF2α and CHOP10. On the other hand, GIV treatment was the only treatment that successfully increased simultaneously BiP, peIF2α, and CHOP10 concentrations.

Bbs12$^{-/-}$ Mouse Retinal Phenotype

Figure 12:
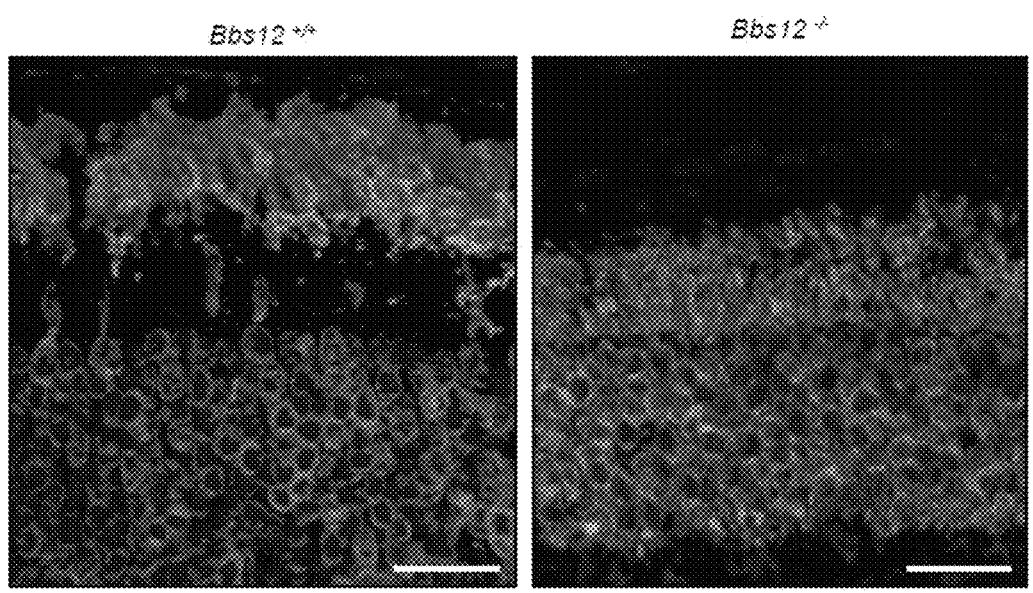
FIG. 12 Arrestin localization in the Bbs12$^{-/-}$ retina. Immunostaining of Arrestin with DAPI co-staining in the Bbs12$^{+/+}$ and Bbs12$^{-/-}$ photoreceptors. Scale bars 20 μm.

Histological studies revealed that Bbs12$^{-/-}$ mice presented photoreceptor degeneration (FIG. 4a). At 10 weeks of age in mutant mice the ONL was thinner and severely disrupted OS were observed using TEM. It appeared that remnant outer segment pieces had disk dilatation and rare residual connecting cilia with a normal 9+0 structure. Scotopic electroretinogram (ERG) recordings evidenced a significant decrease in both a and b waves amplitudes as early as 4 weeks of age. The same recording at 10 weeks of age resulted in a total absence of response to photonic stimuli (FIG. 4b). Both Rhodopsin (FIG. 4c) and Arrestin (FIG. 12) were mislocalized in the ONL and IS, depicting an ICT defect in the Bbs12$^{-/-}$ retina. We measured ER stress gene expression in null retinas. Caspase3 and Caspase12 as well as Chop10 were up-regulated in Bbs12$^{-/-}$ retinas (FIG. 4d). This was accompanied by ER cisternae enlargement (FIG. 4c) in photoreceptor cells.

Kinetics of Apoptosis in the Bbs12$^{-/-}$ Retina

Retinal degeneration was well underway by 4 weeks postnatally. By studying the developmental changes in the abundance of apoptotic nuclei in Bbs12$^{+/+}$ and Bbs12$^{-/-}$ mice, we observed the first BBS12-dependent increase in cell death between postnatal days 12 and 14. Furthermore, expression of Caspase3, Caspase6, Caspase12, Bip, and Chop10 mRNAs was significantly up-regulated in Bbs12$^{-/-}$ retinas at postnatal day 14, which correlated with an increase of BiP and CHOP10 protein contents in the Bbs12$^{-/-}$ retinas. These data validate the ex vivo findings that ER stress is activated in BBS12-deprived retinas.

Figure 5:
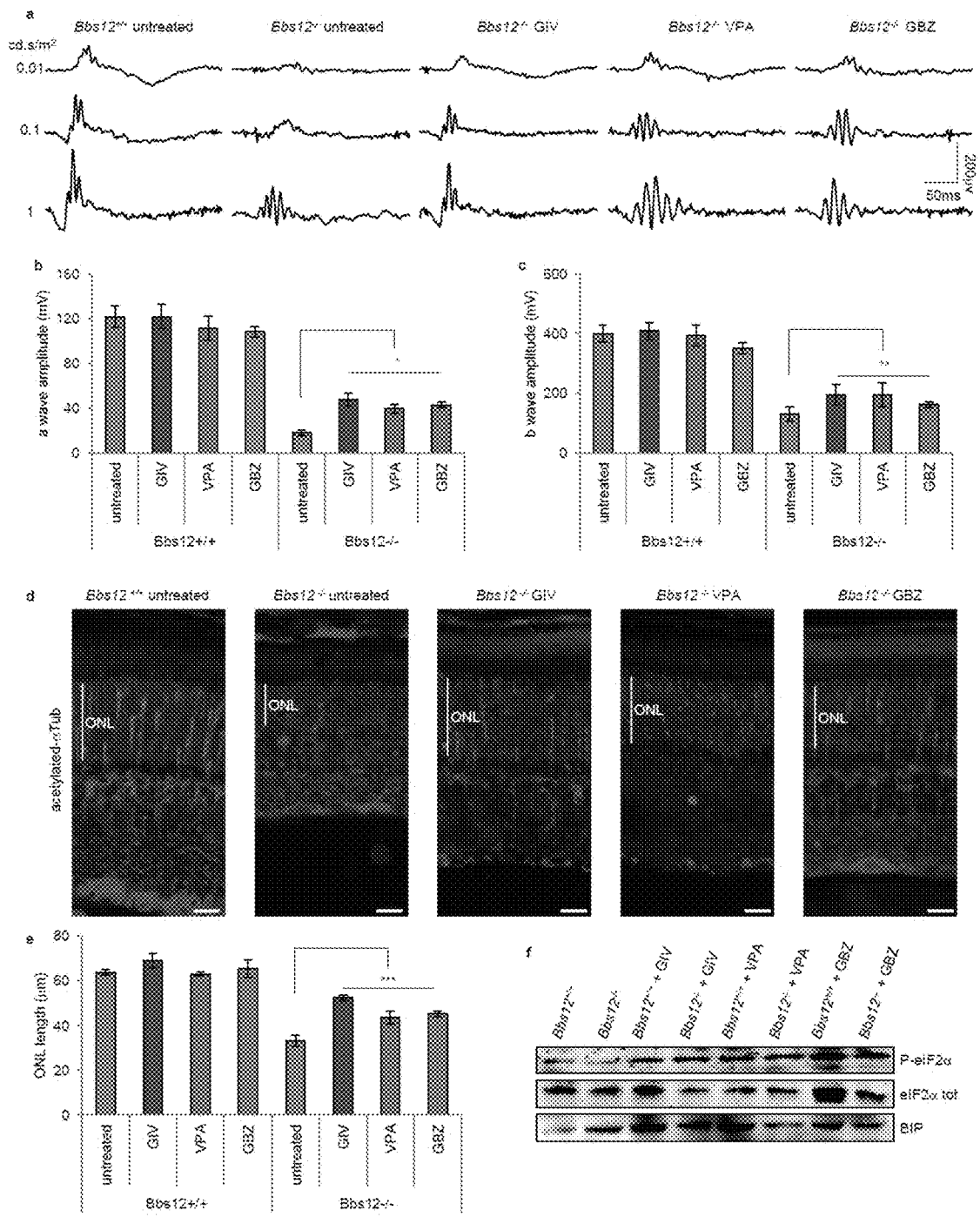
FIG. 5 ER stress treatments restore Bbs12$^{-/-}$ visual function. Comparison of untreated and GIV, VPA or GBZ treated Bbs12$^{+/+}$ and Bbs12$^{-/-}$ animals: (a) Scotopic ERG recording. (b) a wave amplitude at 1 cd·s/m$^2$ scotopic ERG (n=12). *P<0.001. (c) b wave amplitude at 1 cd·s/m$^2$ scotopic ERG (n=12). **P<0.05. (d) Immunostaining of acetylated-α-Tubulin with DAPI co-staining (e) ONL length measured (n=6). *P<0.01. (f) Western blot analysis of phosphorylated and total eIF2α contents and BiP. Scale bars 10 μm.
Figure 6:
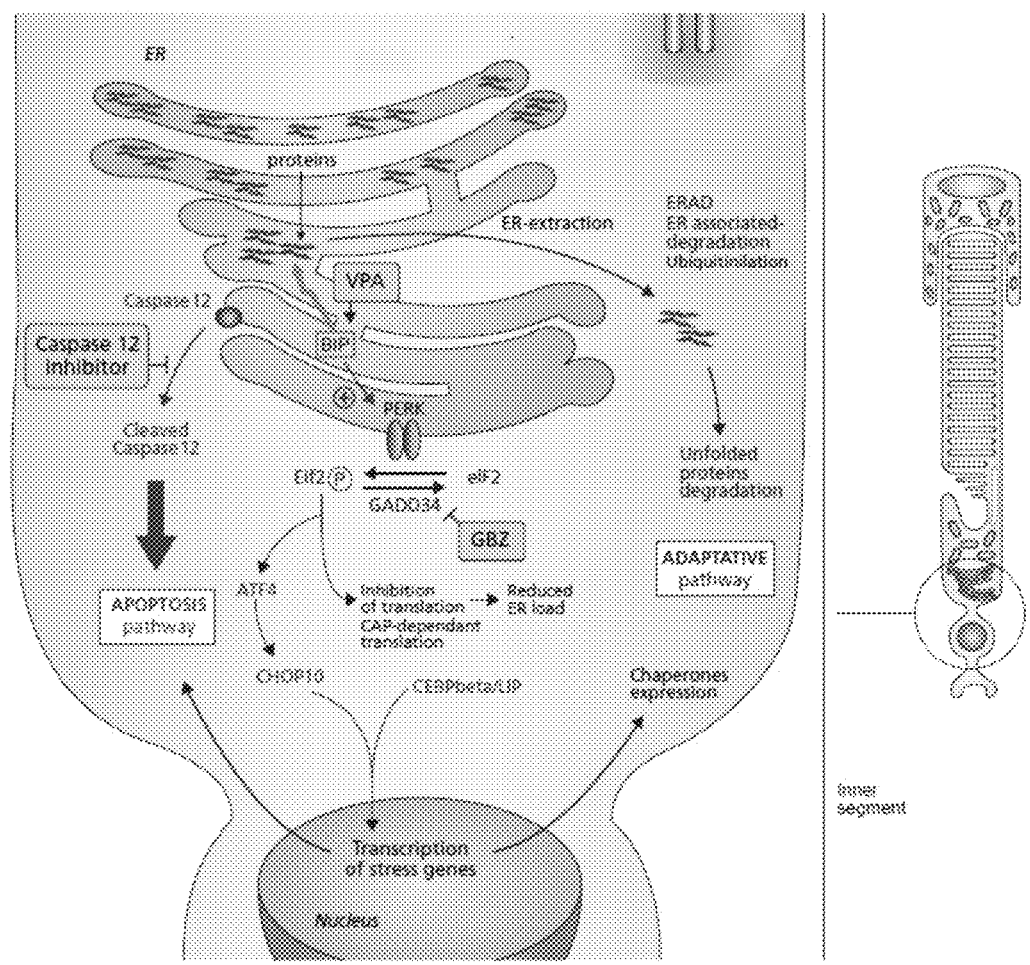
FIG. 6 Proposed mechanism. In the Bbs12$^{-/-}$ retina ICT is not efficient enough, leading to proteins accumulation in the IS. The protein overload induces UPR: the molecular chaperone BiP senses aggregated proteins and activates the eIF2α kinase PERK. eIF2α phosphorylation induces the ER stress response cascade. If homeostasis is not re-established, the proapoptotic response is promoted and leads to apoptosis via caspase-12 activation. We successfully modulated ER stress using VPA to increase BiP content, GBZ to inhibit the eIF2α phosphatase GADD34, and INH to inhibit caspase-12 activity. These synergic treatments reduce photoreceptor apoptosis in the Bbs12$^{-/-}$ mouse.
Figure 13:
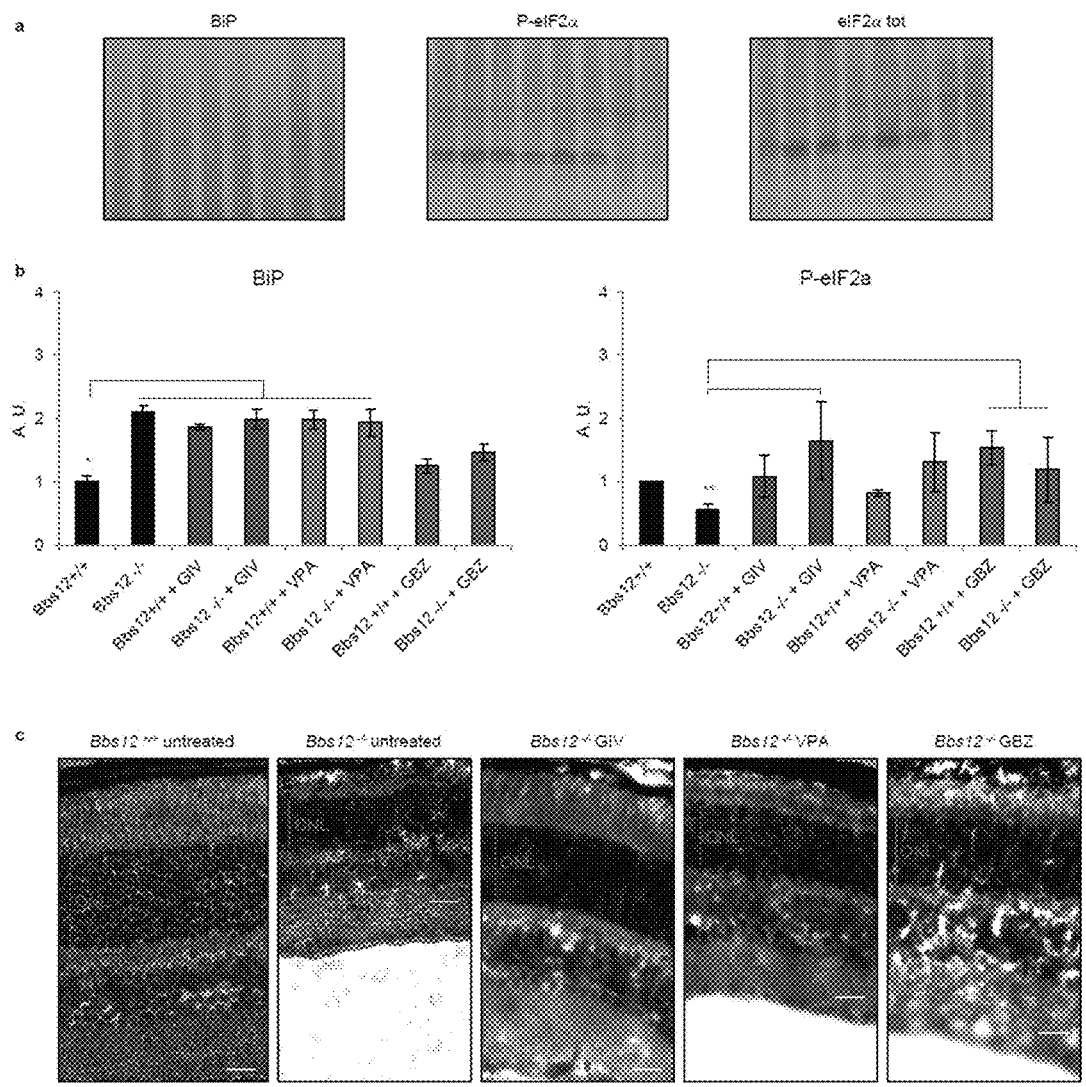
FIG. 13 Analysis of ER stress treatments in animals. (a) Ponceau staining as loading control for Western blots of in Bbs12$^{+/+}$ and Bbs12$^{-/-}$ retinas from mice receiving VPA, GBZ, GIV or no treatment. (b) Corresponding protein quantification (n=3). *P<0.01, **P<0.05 (c) Hematoxylin-Eosine staining of Bbs12$^{+/+}$ and Bbs12$^{-/-}$ retinas from mice receiving VPA, GBZ, GIV or no treatment.

GIV Treatment Protects Photoreceptors from Apoptosis and Restores their Function in Vivo We tested three different kinds of treatment starting at PN14: systemic administration of VPA or GBZ (named VPA and GBZ) and a combined treatment of GBZ and INH in eye drops in addition to a systemic administration of VPA (named GIV). Bbs12$^{-/-}$ mice receiving either GIV, VPA or GBZ treatment presented a clear amelioration in the scotopic ERG recording (FIG. 5a). Both a and b waves amplitudes were significantly increased (FIGS. 5b and 5c and FIGS. 17 and 18). B wave amplitude was also higher in VPA and GIV treated Bbs12$^{-/-}$ animals (FIG. 5c). Acetylated-α-Tubulin immunostaining revealed no improvement in cilia maintenance (FIG. 5d) but showed a significant increase in ONL thickness for treated animals (FIG. 5d). ONL layer thickness was measured: 37 μm for the Bbs12$^{-/-}$ untreated retinas, 52 μm for GIV, 44 μm for VPA and 45 μm for the GBZ treated animals (FIG. 5e and FIG. 13). Moreover, both GIV and GBZ treatments increased the phosphorylated status of eIF2α and GIV and VPA treatment increased BiP protein level (FIG. 5f and FIGS. 13a and 13b).

Discussion

Figure 9:
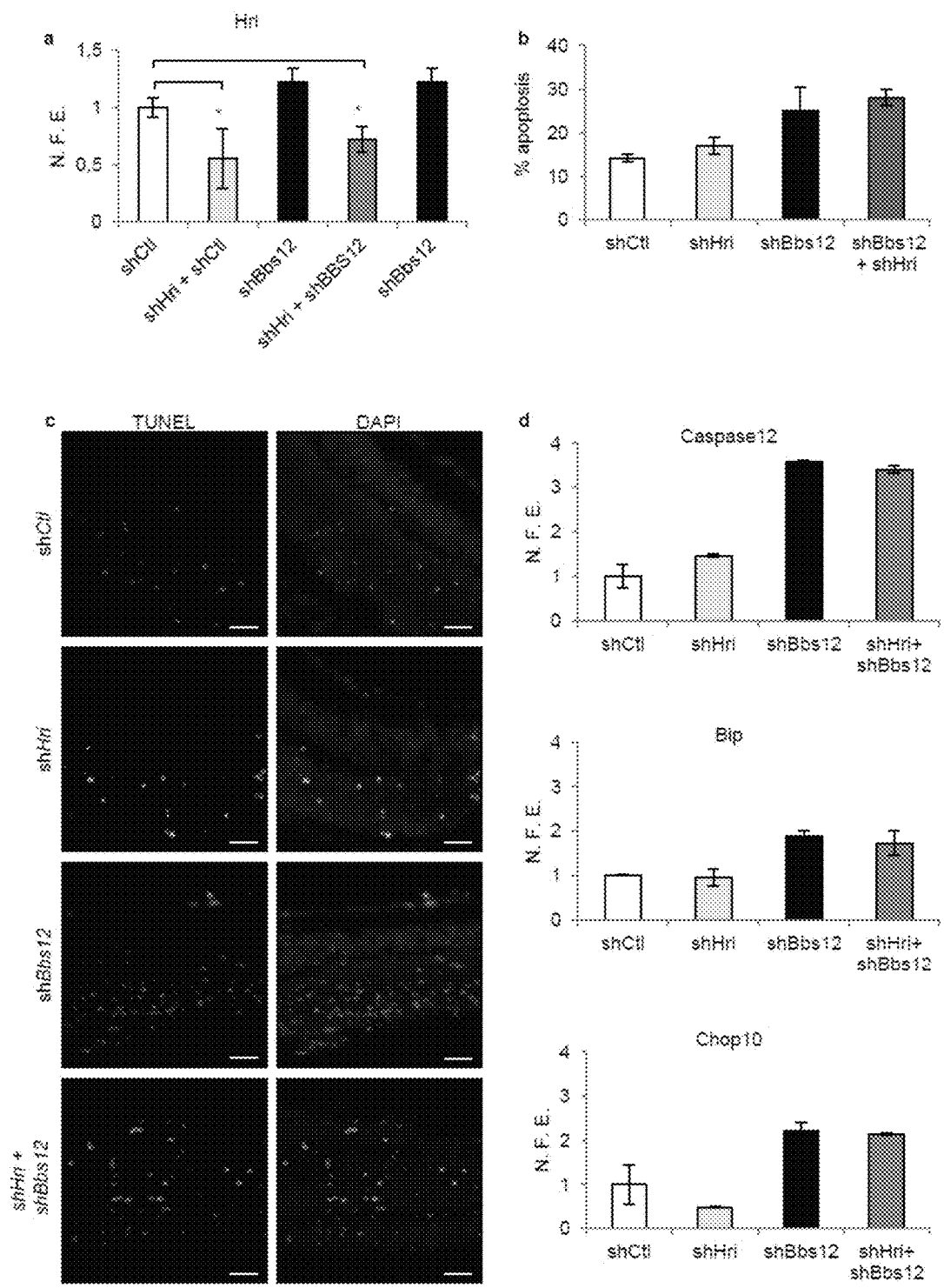
FIG. 9 HRI is not induced by Bbs12 depletion. Synergic depletion of Bbs12 and Hri in retinal explants: (a) Hri mRNA expression (n=3). *P<0.03. (b) Apoptotic rate (n=3), (c) TUNEL assays, (d) Expression analysis of Caspase12, Bip and Chop10 (n=3). Scale bars 25 μm.

Using retinal explant cultures, we dissected the mechanisms leading to photoreceptor apoptosis in the absence of Bbs12. This model presents OS molecule accumulation in the IS, highlighting massive ICT defects in the photoreceptor. Protein accumulation in the IS has led us to investigate ER stress, which is known to be triggered by pathological accumulation of proteins in the lumen of the ER. Three different transducers can mediate UPR via different pathways (Walter et al., 2011): ATF6 (activating transcription factor 6) by transcriptional regulation, PERK by decrease of protein load and IRE1 (inositol requiring enzyme 1) by mRNA degradation. In our model, UPR response was driven by PERK, as we highlighted eIF2α phosphorylation, specific from PERK-mediated UPR response. But other cellular stresses can induce eIF2α phosphorylation: 4 kinases are known (named EIF2AK 1-4, also known as PERK, HRI PKR and GCN2). PERK is related to UPR (Harding et al., 2000), GCN2 is activated in amino acid starvation and UV damage conditions (Harding et al., 2000), HrI is activated during oxidative stress and heme deprivation (Berlanga et al., 1998) and PKR activation is induced by viral infection (Lu et al., 1999). As shCtl and shBbs12 explants were both treated with the same viral titer, we assumed that PKR was not the involved kinase. The culture conditions excluded the activation of GCN2 as the medium was rich enough to avoid amino acid starvation. We could not have excluded an oxidative stress to be at the origin of the photoreceptor cell death. We performed double knockdown of Bbs12 and Hri and no significant changes in assessed genes or apoptotic rate were observed (FIG. 9). At the opposite, we demonstrated that PERK inactivation abrogated ER stress mediation, depicting UPR-induced eIF2α phosphorylation.

We also used an in vivo model: the Bbs12$^{-/-}$ mouse exhibiting retinal dystrophy. It presents the same defects as the ex-vivo model including protein accumulation in the IS, disk dilatation and OS degradation as early as 4 weeks of age. It also presents UPR activation. Other inherited RP animal models have been reported to be linked to ER stress. Indeed, ER stress activation was described for the rd1 mouse (Yang et al., 2007), carrying a mutation in the Pde6b gene and in the P23H Rhodopsin transgenic rat model, causing its misfolding (Lin et al., 2007). Moreover, RP models have been used for therapeutic purposes, highlighting the opportunities of ER stress as a therapeutic target. The first proposed strategy was to modulate ER stress by use of molecular chaperones such as 9-cis-retinal and 11-cis-retinal that successfully restore Rhodopsin folding in a cellular model (Mendes et al., 2008). Then it was proposed to directly modulate UPR actors. Thus, overexpression of BiP in the P23H Rhodopsin rat model restores visual function (Gorbatyuk et al., 2010), demonstrating the efficacy of ER stress modulation for RP treatment. Recently, tauroursodeoxycholic acid (TUDCA) was used to treat Bbs1$^{M390R/M390R}$ mice (Drack et al., 2012). TUDCA was described in this study as an anti-apoptotic compound, and induced retinal thickening in treated animals. In fact, in the literature, TUDCA is known as a chemical chaperone, able to enhance the adaptative capacity of the ER in UPR condition (De Almeida et al., 2007; Ozcan et al., 2006).

We chose as a therapeutic strategy to use the combination of three compounds known to modulate ER. The first is VPA, used as an anti-convulsant and a mood stabilizer. It is described to modulate BiP transcription (Wang et al., 1999), probably via its HDAC inhibitor activity, and it has been also proposed to modulate interaction of ER chaperones with co-activators (Kakuichi et al., 2009; Penas et al., 2011). VPA treatment was already used in several studies of retinal diseases as a neuroprotective agent: it is efficient for retinal ganglion cell protection after optic nerve crushing by delaying cell death and decreasing Caspase3 activation (Biermann et al., 2010). It has been shown to protect retinal cells against apoptosis induced by ischemia-reperfusion injury in rats (Zhang et al., 2011). Indeed, this stress induces ER-stress mediated apoptosis of retinal neurons and systemic VPA administration increased BiP expression and reduced caspase-12 activation in the rat retina. VPA was also used in a clinical trial for RP patients linked to Rhodopsin misfolding. This controversial study showed an increase of visual field in 5 to 7 patients treated for 2 or 4 months with VPA (Clemson et al., 2011). On an other hand, GBZ, an α-adrenergic receptor agonist, is used for hypertension treatment (Holmes et al., 1983). It was also reported to have anti-prion activity (Tribouillard-Tanvier et al., 2008) and was recently identified as an inhibitor of GADD34, the eIF2alpha phosphatase (Tsaytler et al., 2011). GBZ treatment can reduce global protein load by maintaining eIF2α in its inactive form. To be more efficient in this abrogation of ER stress, we added an anti-apoptotic molecule: a peptide designed to specifically inhibit Caspase12 activity. The combined treatments allowed us to trigger ER stress at different levels of the cellular response and successfully reduced photoreceptor apoptosis in Bbs12-depleted explants.

Figure 14:
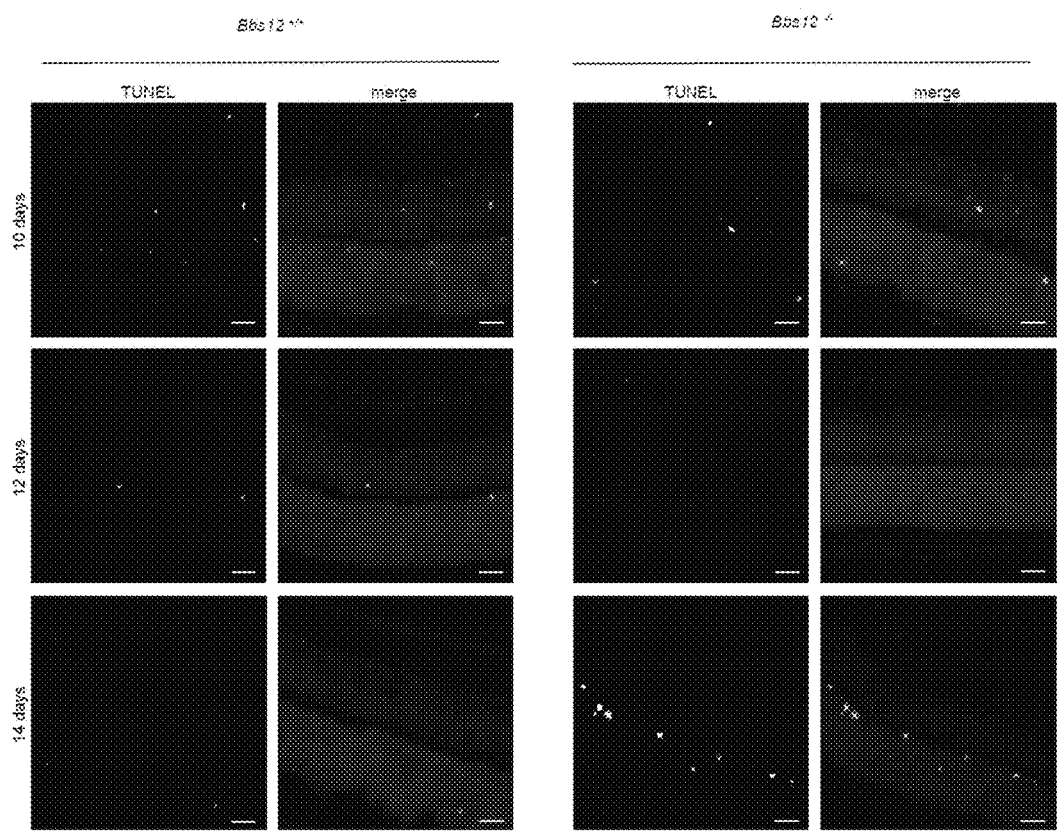
FIG. 14 Apoptosis kinetic in the Bbs12$^{-/-}$ retina. TUNEL assays in Bbs12$^{+/+}$ and Bbs12$^{-/-}$ retinas at post-natal days 10, 12 and 14, scale bars 25 μm.
Figure 15:
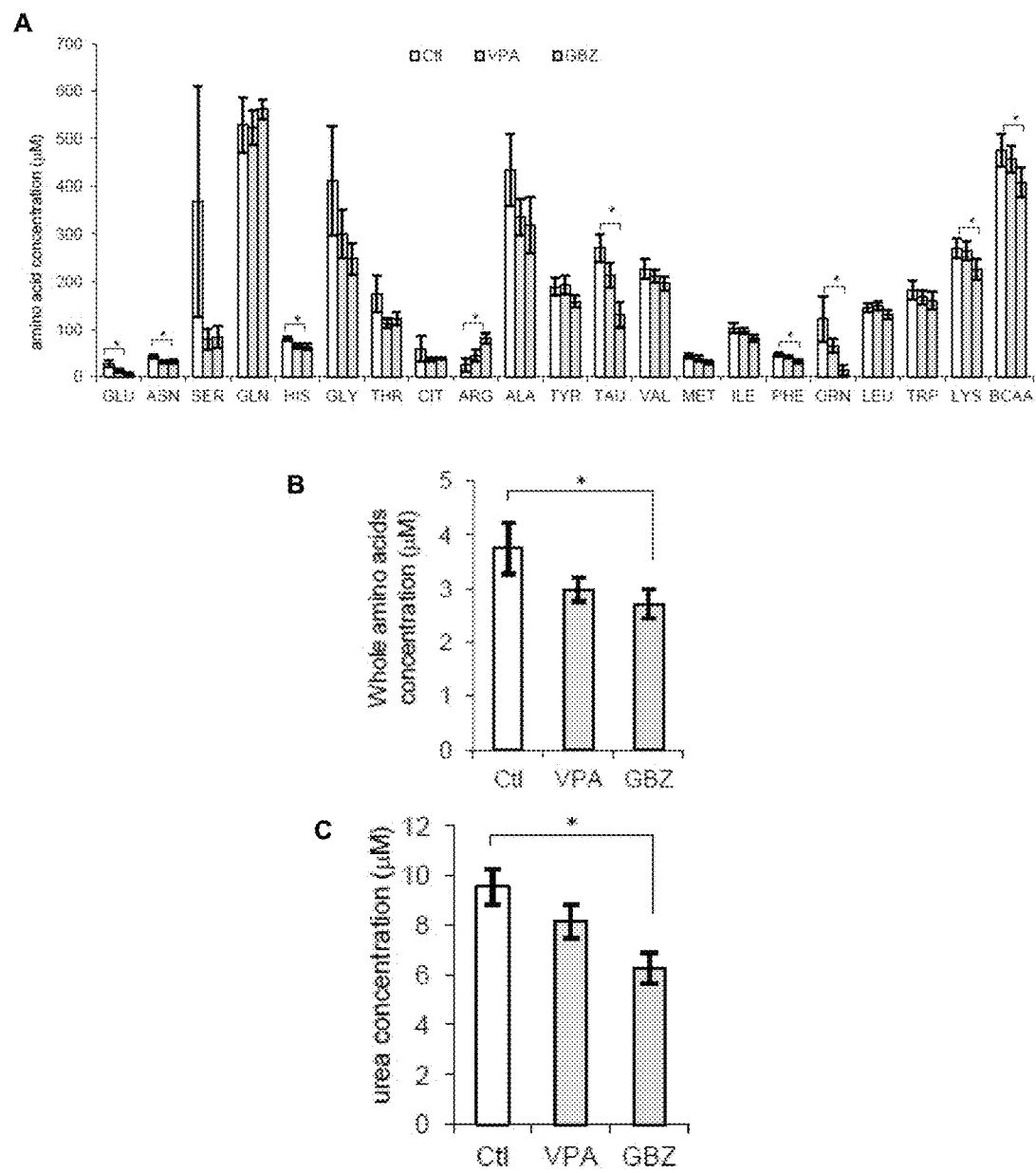
FIG. 15 Impact of systemic drug treatment on hepatic function. Analysis of plasma content of wt animals treated for 10 weeks with either DMSO 0.003% (CTL) or VPA or GBZ: (a) amino acid concentrations (glutamic acid, asparagine, serine, glutamine, histidine, glycine, threonine, cysteine, arginine, alanine, tyrosine, valine, methionine, isoleucine, phenylalanine, ornithine, leucine, tryptophan, lysine and branched-chain amino acids); (b) whole amino acid concentration; (c) unlabeled urea concentration after 2 hours of perfusion of labeled urea, proportional to the urea clearance rate. *P<0.05.
Figure 16:
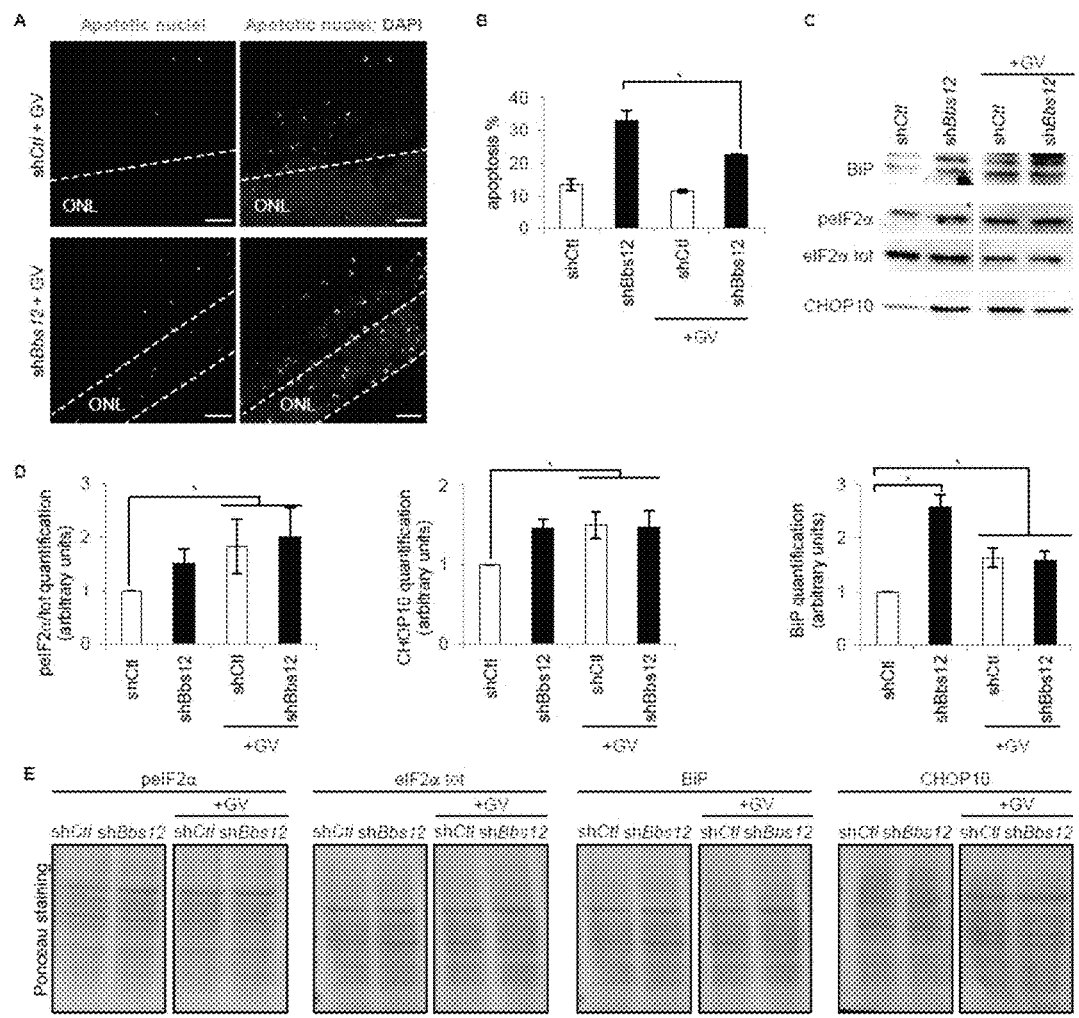
FIG. 16 GV treatment in retinal explants. (A) TUNEL assays in shCtl and shBbs12 explants receiving GV treatment (Scale bars: 20 mm). (B) Apoptotic levels of indicated-treated explants. (C) Immunodetection of BiP, peIF2α, eIF2αtot and CHOP10 in the indicated shRNA-treated explants supplemented or not with GV. (D) Protein quantification; untreated retinas loaded on the same gel were used as standard. (E) Ponceau staining as loading control for Western blots of treated explants. GV: GBZ 2.5 μM+VPA 0.2 mM.
Figure 17:
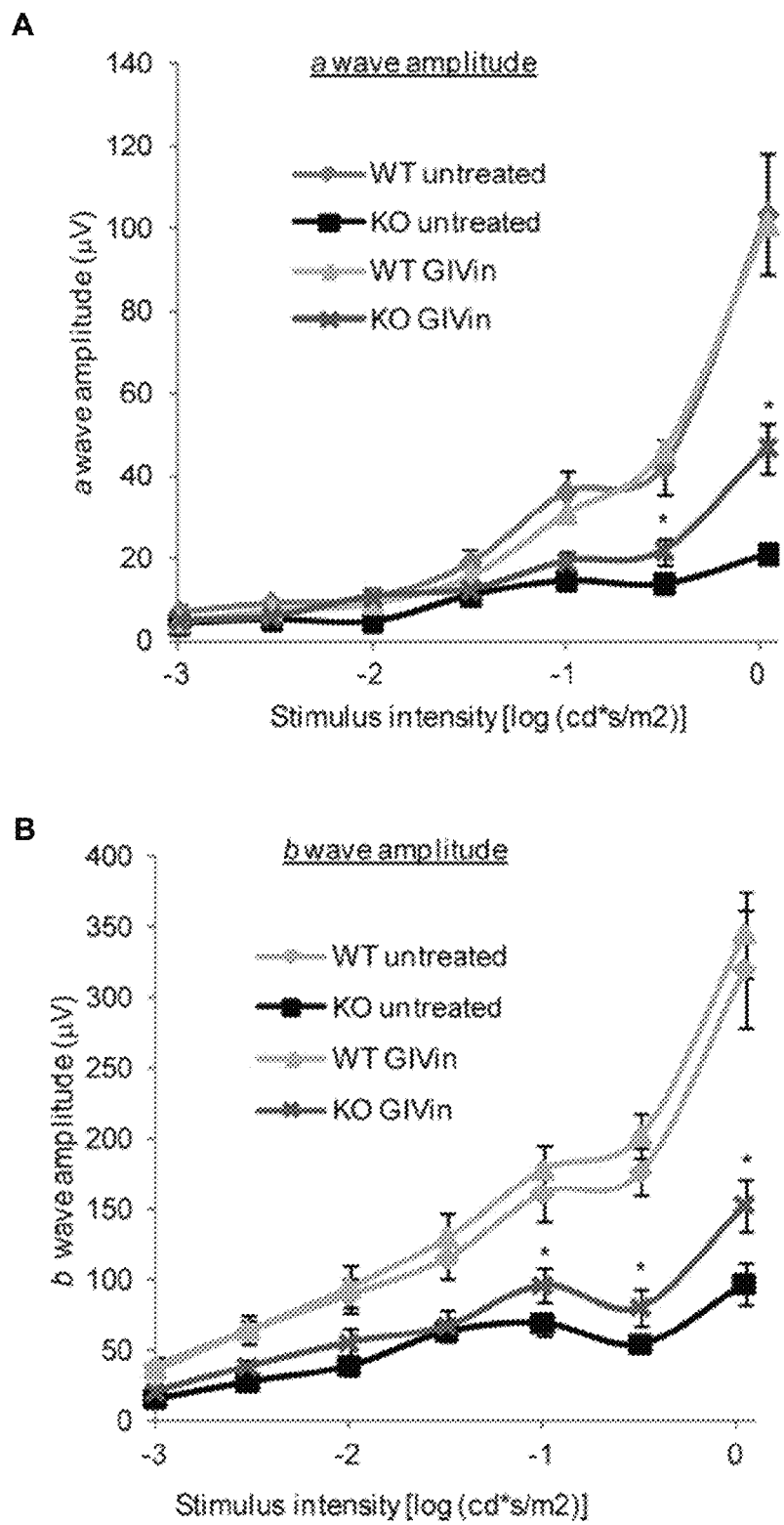
FIG. 17: Pharmacological modulation of UPR prevents photoreceptor loss in Bbs12$^{-/-}$ retinas. (A) Scotopic a-wave amplitude versus stimulus intensity (log) function of animals with indicated treatment and genotype at 4 weeks of age (n=12). *, p<0.05. (B) scotopic b-wave amplitude versus stimulus intensity (log) function of indicated animals (n=12). **, p<0.05. The animals were treated for 2 weeks with GIVin: topical GBZ 7.5 μM+topical INH 500 μM+systemic VPA 5 mg/ml.

The characterization of the retinal phenotype of the Bbs12$^{-/-}$ mice revealed that the degeneration is almost achieved at 4 weeks of age. As determination of the apoptotic kinetic was essential for in vivo treatments, we validated that cell death starts when the connecting cilium grows and the OS begins to form, at 14 days post-natal (PN14) (FIG. 14). PN14 was chosen as the starting point for retinal treatments. To assess if systemic administration of VPA and GBZ might have toxic effects, we treated wt mice for 10 weeks with VPA or GBZ and hepatic function was assed using plasma amino acid concentrations and urea clearance measurements. It appeared that VPA treatment induced no significant changes in hepatic function whereas GBZ had a deleterious impact (FIG. 15). As GBZ was already successfully used in eye drops for treatment of rat AMD models (Shen et al., 2011), we preferred to combine it with INH in eye drop solution for GIV treatment. The treatments in vivo have shown promising results: treated Bbs12$^{-/-}$ animals present more remnant photoreceptor cells and animals have a clear amelioration in the ERG recording. In aggregate, the in vivo studies suggest that GBZ and VPA treatments are efficient to reduce photoreceptor apoptosis but the combination of the three drugs emphasizes the protective effect as both electrophysiological and histological analysis after GIV treatment present slightly better results.

In this study we report the proof of the principle of retinal degeneration slowdown in a mouse model of BBS using ER-stress modulating drugs. Altogether, retinal ciliopathies represent an important part of inherited RP. As the mechanisms are closely related for the different genes mutated, the GIV treatment rise promising opportunities. Moreover, emerging evidence supports the crucial role of ER stress in the occurrence of photoreceptor apoptosis in different kinds of RP. These results pave the way for an alternative to gene therapy in the field of RP.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

Abd-El-Barr, M. M., et al. Vision Res 47, 3394-3407 (2007).
Beltran et al., Proc Natl Acad Sci USA. 2012 Feb. 7; 109(6):2132-7.
Berlanga, J. J., Herrero, S. & de Haro, C. J Biol Chem 273, 32340-32346 (1998).
Biermann, J., et al. Invest Ophthalmol Vis Sci 51, 526-534 (2010).
Clemson, C. M., et al. Br J Ophthalmol 95, 89-93 (2011).
Cunha et al., Diabetes. 2009 December; 58(12): 2851-2862.
Drack, A. V., et al. Invest Ophthalmol Vis Sci 53, 100-106 (2012).
de Almeida, S. F., et al. J Biol Chem 282, 27905-27912 (2007).
Davis, R. E., et al. Proc Natl Acad Sci USA 104, 19422-19427 (2007).
Fath, M. A., et al. Hum Mol Genet 14, 1109-1118 (2005).
Fliegauf, M., et al, H. Nat Rev Mol Cell Biol 8, 880-893 (2007).
Gorbatyuk, M. S., et al. Proc Natl Acad Sci USA 107, 5961-5966 (2010).
Griciuc, A., Aron, L. & Ueffing, M. Trends Mol Med 17, 442-451 (2011).
Harding, H. P., Zhang, Y., Bertolotti, A., Zeng, H. & Ron, D. Mol Cell 5, 897-904 (2000).
Harding, H. P., et al. Mol Cell 6, 1099-1108 (2000).
Hiroi et al. Pharmacogenomics J. 2005; 5(2):102-11.
Hicks, D. & Molday, R. S. Exp Eye Res 42, 55-71 (1986).
Hallemeesch, M. M., Ten Have, G. A. & Deutz, N. E. Lab Anim 35, 101-110 (2001).
Holmes, B., Brogden, R. N., Heel, R. C., Speight, T. M. & Avery, G. S. Drugs 26, 212-229 (1983).
Jiang et al. Int J Mol Med. 2008 December; 22(6):717-24.
Kosmaoglou, M., Schwarz, N., Bett, J. S. & Cheetham, M. E. Prog Retin Eye Res 27, 434-449 (2008).
Kakiuchi, C., et al. PLoS One 4, e4134 (2009).
Kudo et al. Cell Death Differ. 2008 February; 15(2):364-75.
Lu, J., O'Hara, E. B., Trieselmann, B. A., Romano, P. R. & Dever, T. E. J Biol Chem 274, 32198-32203 (1999).
Lin, J. H., et al. Science 318, 944-949 (2007).
Mendes, H. F. & Cheetham, M. E. Hum Mol Genet 17, 3043-3054 (2008).
Mitsuhashi et al. J Biol Chem. 2003 Jan. 3; 278(1):82-8
Mockel, A., et al. Prog Retin Eye Res 30, 258-274 (2011).
Mykytyn, K., et al. Proc Natl Acad Sci USA 101, 8664-8669 (2004).
Nishimura, D. Y., et al. Proc Natl Acad Sci USA 101, 16588-16593 (2004).
Nachury, M. V., et al. Cell 129, 1201-1213 (2007).
Ozcan, U., et al. Science 313, 1137-1140 (2006).
Penas, C., et al. Neuroscience 178, 33-44 (2011).
Pretorius, P. R., et al. PLoS Genet 6, e1000884 (2010).
Reidel, B., Orisme, W., Goldmann, T., Smith, W. C. & Wolfrum, U. Vision Res 46, 4464-4471 (2006).
Seo, S., et al. Proc Natl Acad Sci USA 107, 1488-1493 (2010).
Shen, Y., Zhuang, P. & Chiou, G. C. Open Ophthalmol J 5, 27-31 (2011).
Shi et al. Bioorg Med Chem Lett. 2007 Aug. 15; 17(16): 4491-4.
Simons et al., Proc Natl Acad Sci USA. 2011 Apr. 12; 108(15):6276-81.
Tam, B. M. & Moritz, O. L. Invest Ophthalmol Vis Sci 47, 3234-3241 (2006).
Tsaytler et al. Science. 2011 Apr. 1; 332(6025):91-4
Tribouillard-Tanvier, D., et al. PLoS One 3, e1981 (2008).
van Eijk, H. M., Rooyakkers, D. R. & Deutz, N. E. J Chromatogr 620, 143-148 (1993).
Walter, P. & Ron, D. Science 334, 1081-1086 (2011).
Wang, J. F., Bown, C. & Young, L. T. Mol Pharmacol 55, 521-527 (1999).
Yang, L. P., et al. (2007). Invest Ophthalmol Vis Sci 48, 5191-5198.
Zhang, Z., et al. Neurosci Lett 504, 88-92 (2011).

The invention claimed is:

1. A method of treating retinal degeneration induced by Bardet-Biedl syndrome or by Leber's congenital amaurosis caused by mutation in a ciliary gene, the method comprising administering guanabenz and valproic acid to a subject having retinal degeneration induced by Bardet-Biedl syndrome or by Leber's congenital amaurosis caused by mutation in a ciliary gene.

2. The method of claim 1, further comprising the administration of an inhibitor of caspase-12.

3. The method of claim 1, wherein the method comprises administering guanabenz and valproic acid topically, orally, intradermally, parenterally or intraocularly.

4. The method of claim 1, wherein said method comprises topical ocular or peri-ocular administration of said guanabenz and said valproic acid.

5. The method of claim 2, wherein the inhibitor of caspase 12 is a peptide of formula Ala-Thr-Ala-Asp(OMe)-fluoromethyl ketone (SEQ ID NO: 3).

* * * * *

UNITED STATES PATENT AND TRADEMARK OFFICE
CERTIFICATE OF CORRECTION

PATENT NO. : 9,636,377 B2
APPLICATION NO. : 14/380493
DATED : May 2, 2017
INVENTOR(S) : Vincent Marion, Anaïs Mockel and Hélène Dollfus It is certified that error appears in the above-identified patent and that said Letters Patent is hereby corrected as shown below:

In the Specification

Column 4,
Line 45, "25 P<0.05." should read --25 µm. $P<0.05$.--.

Column 7,
Line 6, "and Bbse)" should read --and $Bbs6^{-/-}$)--.

Column 20,
Line 56, "One of total" should read --One µg of total--.

Column 22,
Line 6, "anti-O-Tubulin" should read --anti-β-Tubulin--.

Column 22,
Lines 7-8, "anti-β-Tubulin" should read --anti-γ-Tubulin--.

Column 22,
Line 9, "anti-acetylated-β-Tubulin" should read --anti-acetylated-α-Tubulin--.

Figure 10:
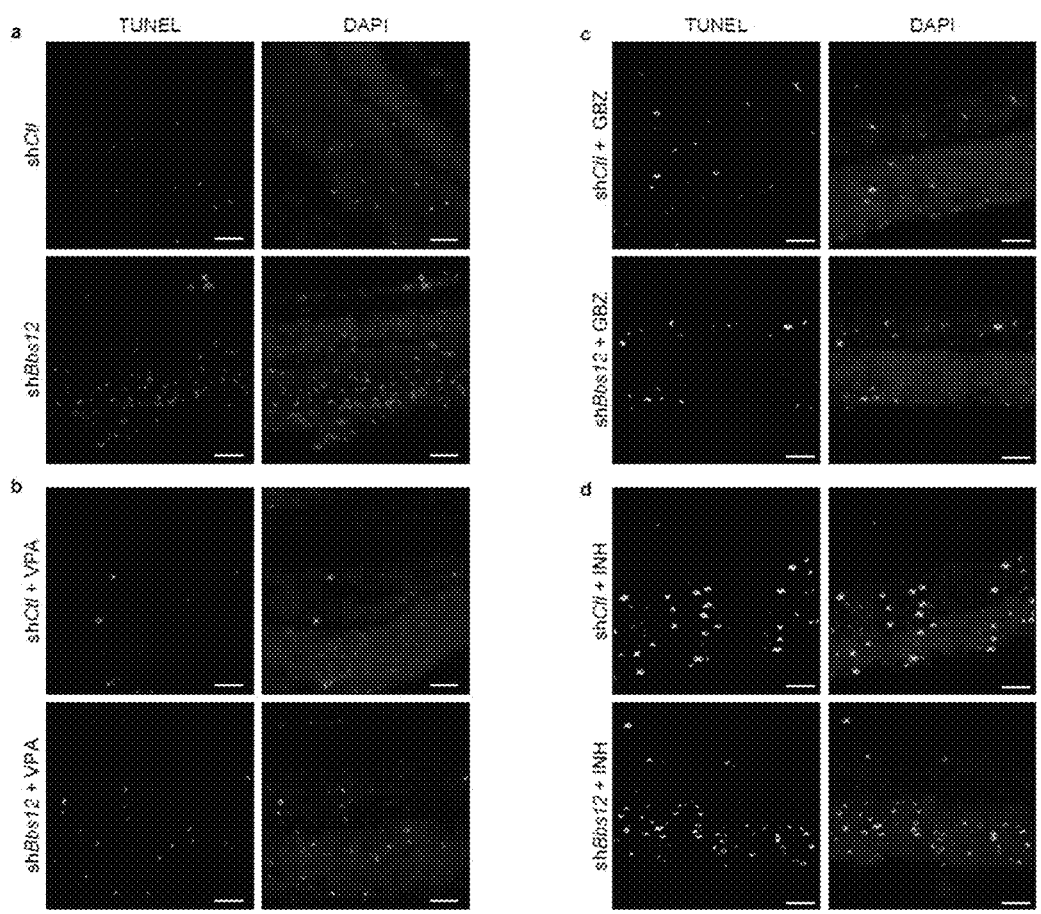
FIG. 10 TUNEL assays for ER stress treatment in retinal explants. TUNEL assays in shCtl and shBbs12 treated explants without treatment (a), with VPA treatment (b), with GBZ treatment (c), with INH treatment (d). Scale bars 25 μm.
Figure 11:
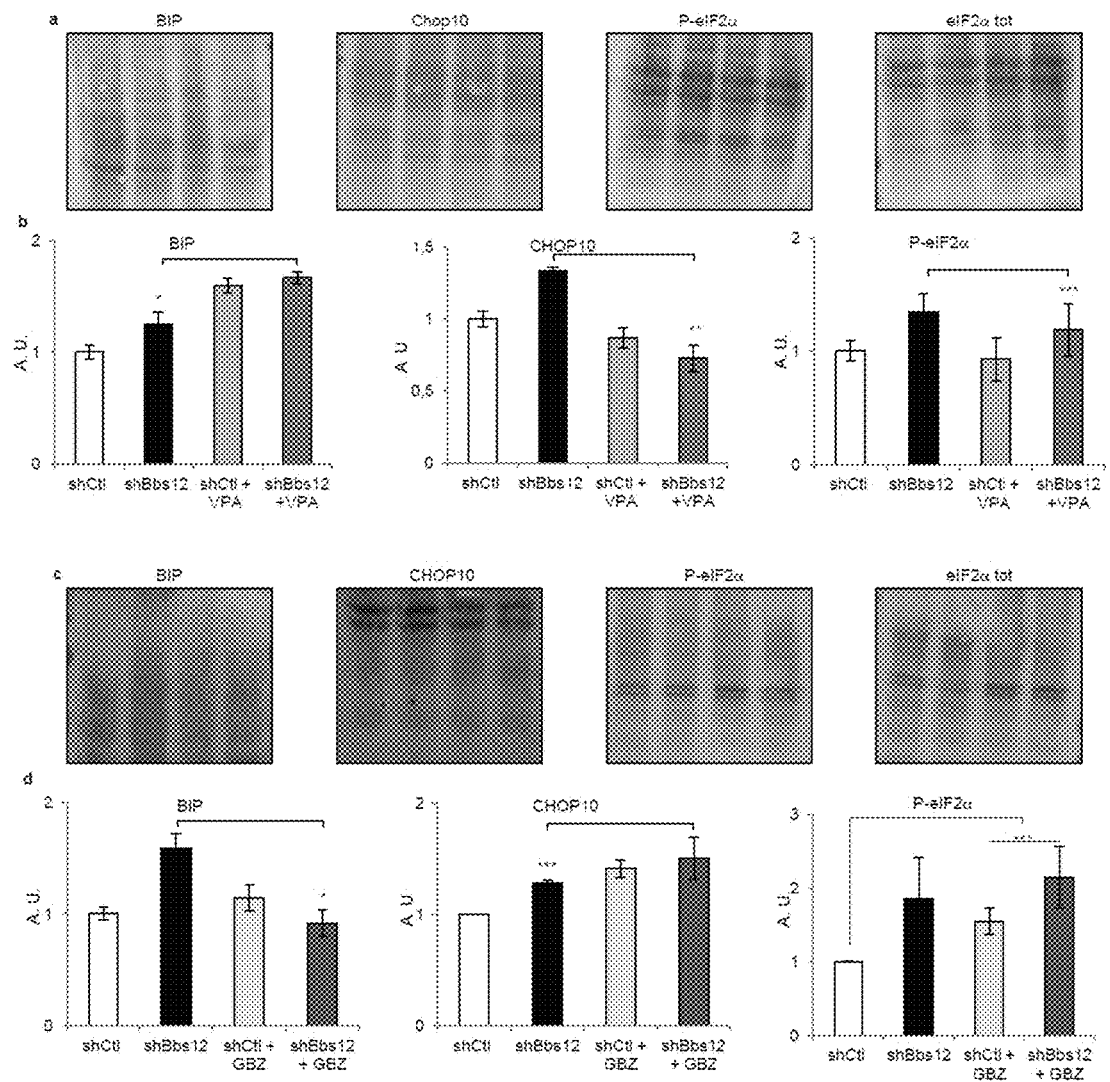
FIG. 11 Western blot analysis for ER stress treatment in retinal explants. (a) Ponceau staining as loading control for Western blots of shCtl and shBbs12 treated explants supplemented with VPA. (b) Corresponding protein quantification (n=3). *P<0.05, P<0.05, *P<0.1. (c) Ponceau staining as loading control for Western blots of shCtl and shBbs12 treated explants supplemented with GBZ. (d) Corresponding proteins quantification (n=3). *P<0.05, ***P<0.05.

Column 23,
Line 19, "(FIG. 10." should read --(Fig. 1f).--.

Column 24,
Line 21, "and 1 in" should read --and 1 µM, in--.

Column 25,
Line 39, "Hill is" should read --HRI is--.

Signed and Sealed this
Twenty-third Day of January, 2018

Joseph Matal
*Performing the Functions and Duties of the
Under Secretary of Commerce for Intellectual Property and
Director of the United States Patent and Trademark Office*